(12) United States Patent
Vogel et al.

(10) Patent No.: US 8,409,814 B2
(45) Date of Patent: Apr. 2, 2013

(54) SENSOR PROTEINS AND ASSAY METHODS

(75) Inventors: Kurt Vogel, Madison, WI (US); Rhonda Newman, Eugene, OR (US); Steven Riddle, Madison, WI (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 12/874,140

(22) Filed: Sep. 1, 2010

(65) Prior Publication Data

US 2011/0111422 A1 May 12, 2011

Related U.S. Application Data

(63) Continuation of application No. 11/837,180, filed on Aug. 10, 2007, now abandoned.

(60) Provisional application No. 60/822,206, filed on Aug. 11, 2006.

(51) Int. Cl.
*G01N 33/53* (2006.01)
*G01N 33/00* (2006.01)
*C07K 1/00* (2006.01)
*C07K 14/00* (2006.01)
*C07K 16/00* (2006.01)
*C07K 17/00* (2006.01)

(52) U.S. Cl. ......... 435/7.1; 436/103; 530/400; 530/402; 530/408; 530/409; 530/410

(58) Field of Classification Search ........................ None
See application file for complete search history.

(56) References Cited

U.S. PATENT DOCUMENTS

| | | | | |
|---|---|---|---|---|
| 5,254,477 | A | * | 10/1993 | Walt .............................. 436/172 |
| 5,304,472 | A | | 4/1994 | Bass et al. |
| 5,898,069 | A | * | 4/1999 | Webb et al. ................ 530/388.9 |
| 6,197,928 | B1 | | 3/2001 | Tsien et al. |
| 6,900,304 | B2 | | 5/2005 | Tsien et al. |
| 2005/0054573 | A1 | * | 3/2005 | Werner et al. .................... 514/12 |
| 2005/0112685 | A1 | | 5/2005 | Amiss et al. |

FOREIGN PATENT DOCUMENTS

WO WO-2007/044014 4/2007

OTHER PUBLICATIONS

Hirshberg et al. Crystal Structure of Phosphate Binding Protein Labeled with a Coumarin Fluorophore, a Probe for Inorganic Phosphate. Biochemistry, 1998, vol. 37, pp. 10381-10385.*
Sapsford et al. Materials for Fluorescence Resonance Energy Transfer Analysis: Beyond Traditional Donor-Acceptor Combinations. Angew. Chem. Int. Ed. 2006, vol. 45, pp. 4562-4588.*
07873959.6, "Extended European Search Report", mailed Feb. 22, 2010, 4 pgs.
De Lorimier, R. M. "Construction of a fluorescent biosensor family", *Protein Science* vol. 11(11), 2002, 2655-2675.
Gu, H. "Design of phosphate nanosensors", *Riso publication database* 2006, 1-2.
Magota, K. "Nucleotide sequence of the *phoS* gene, the structural gene for the phosphate-binding protein of *Escherichia coli*", *J. Bacteriol.* vol. 157(3) 1984, 909-917.
PCT/US20071075705, "PCT international search report" mailed Jan. 16, 2009, 4 pgs.
Pickup, J. C. "Fluorescence-based glucose sensors", *Biosensors and Bioelectronics*, vol. 20, 2005, 2555-2565.
Riddle, S. M. "Time-resolved fluorescence resonance energy transfer kinase assays using physiological protein substrates: Applications of terbium-fluorescein and terbium-green fluorescent protein fluorescence resonance energy transfer pairs", *Analytical Biochemistry* vol. 356(1), 2006, 108-116.
Surin, B. P. "Phosphate-specific transport system of *Escherichia coli*: Nucleotide sequence and gene-polypeptide relationships", *J. Bacteriol.*, vol. 161 (1), 1985, 189-198.

* cited by examiner

*Primary Examiner* — Marcela M Cordero Garcia

(57) ABSTRACT

The present invention relates to biosensors. In some embodiments, the biosensors are modified ligand binding molecules. In some embodiments, the modified ligand binding molecule is a phosphate binding protein (PBP). In some embodiments, the modified ligand binding molecules are labeled to be capable of RET, e.g., comprising a donor and acceptor moiety. In some embodiments of the invention, there is a detectable change in RET (e.g., FRET) when the modified ligand binding molecule binds and/or releases the ligand (e.g., phosphate). The invention also provides related methods, reactions and assays.

20 Claims, 17 Drawing Sheets

SEQUENCE LISTING

<160> NUMBER OF SEQ ID NOS: 5

<210> SEQ ID NO 1
<211> LENGTH: 346
<212> TYPE: PRT
<213> ORGANISM: Escherichia coli

<400> SEQUENCE: 1

```
Met Lys Val Met Arg Thr Thr Val Ala Thr Val Ala Ala Thr Leu
 1               5                  10                  15

Ser Met Ser Ala Phe Ser Val Phe Ala Glu Ala Ser Leu Thr Gly Ala
                20                  25                  30

Gly Ala Thr Phe Pro Ala Pro Val Tyr Ala Lys Trp Ala Asp Thr Tyr
                35                  40                  45

Gln Lys Glu Thr Gly Asn Lys Val Asn Tyr Gln Gly Ile Gly Ser Ser
        50                  55                  60

Gly Gly Val Lys Gln Ile Ile Ala Asn Thr Val Asp Phe Gly Ala Ser
 65                  70                  75                  80

Asp Ala Pro Leu Ser Asp Glu Lys Leu Ala Gln Glu Gly Leu Phe Gln
                85                  90                  95

Phe Pro Thr Val Ile Gly Gly Val Val Leu Ala Val Asn Ile Pro Gly
                100                 105                 110

Leu Lys Ser Gly Glu Leu Val Leu Asp Gly Lys Thr Leu Gly Asp Ile
                115                 120                 125

Tyr Leu Gly Lys Ile Lys Lys Trp Asp Asp Glu Ala Ile Ala Lys Leu
        130                 135                 140

Asn Pro Gly Leu Lys Leu Pro Ser Gln Asn Ile Ala Val Val Arg Arg
145                 150                 155                 160

Ala Asp Gly Ser Gly Thr Ser Phe Val Phe Thr Ser Tyr Leu Ala Lys
                165                 170                 175

Val Asn Glu Glu Trp Lys Asn Asn Val Gly Thr Gly Ser Thr Val Lys
                180                 185                 190

Trp Pro Ile Gly Leu Gly Gly Lys Gly Asn Asp Gly Ile Ala Ala Phe
        195                 200                 205

Val Gln Arg Leu Pro Gly Ala Ile Gly Tyr Val Glu Tyr Ala Tyr Ala
        210                 215                 220

Lys Gln Asn Asn Leu Ala Tyr Thr Lys Leu Ile Ser Ala Asp Gly Lys
225                 230                 235                 240

Pro Val Ser Pro Thr Glu Glu Asn Phe Ala Asn Ala Lys Gly Ala
                245                 250                 255

Asp Trp Ser Lys Thr Phe Ala Gln Asp Leu Thr Asn Gln Lys Gly Glu
                260                 265                 270

Asp Ala Trp Pro Ile Thr Ser Thr Phe Ile Leu Ile His Lys Asp
                275                 280                 285

Gln Lys Lys Pro Glu Gln Gly Thr Glu Val Leu Lys Phe Phe Asp Trp
        290                 295                 300

Ala Tyr Lys Thr Gly Ala Lys Gln Ala Asn Asp Leu Asp Tyr Ala Ser
305                 310                 315                 320

Leu Pro Asp Ser Val Val Glu Gln Val Arg Ala Ala Trp Lys Thr Asn
                325                 330                 335

Ile Lys Asp Ser Ser Gly Lys Pro Leu Tyr
        340                 345
```

<210> SEQ ID NO 2

```
<211> LENGTH: 321
<212> TYPE: PRT
<213> ORGANISM: Escherichia coli

<400> SEQUENCE: 2

Glu Ala Ser Leu Thr Gly Ala Gly Ala Thr Phe Pro Ala Pro Val Tyr
 1               5                  10                  15

Ala Lys Trp Ala Asp Thr Tyr Gln Lys Glu Thr Gly Asn Lys Val Asn
                20                  25                  30

Tyr Gln Gly Ile Gly Ser Ser Gly Gly Val Lys Gln Ile Ile Ala Asn
             35                  40                  45

Thr Val Asp Phe Gly Ala Ser Asp Ala Pro Leu Ser Asp Glu Lys Leu
 50                  55                  60

Ala Gln Glu Gly Leu Phe Gln Phe Pro Thr Val Ile Gly Gly Val Val
 65                  70                  75                  80

Leu Ala Val Asn Ile Pro Gly Leu Lys Ser Gly Glu Leu Val Leu Asp
                 85                  90                  95

Gly Lys Thr Leu Gly Asp Ile Tyr Leu Gly Lys Ile Lys Lys Trp Asp
            100                 105                 110

Asp Glu Ala Ile Ala Lys Leu Asn Pro Gly Leu Lys Leu Pro Ser Gln
        115                 120                 125

Asn Ile Ala Val Val Arg Arg Ala Asp Gly Ser Gly Thr Ser Phe Val
130                 135                 140

Phe Thr Ser Tyr Leu Ala Lys Val Asn Glu Glu Trp Lys Asn Asn Val
145                 150                 155                 160

Gly Thr Gly Ser Thr Val Lys Trp Pro Ile Gly Leu Gly Gly Lys Gly
                165                 170                 175

Asn Asp Gly Ile Ala Ala Phe Val Gln Arg Leu Pro Gly Ala Ile Gly
            180                 185                 190

Tyr Val Glu Tyr Ala Tyr Ala Lys Gln Asn Asn Leu Ala Tyr Thr Lys
        195                 200                 205

Leu Ile Ser Ala Asp Gly Lys Pro Val Ser Pro Thr Glu Glu Asn Phe
210                 215                 220

Ala Asn Ala Ala Lys Gly Ala Asp Trp Ser Lys Thr Phe Ala Gln Asp
225                 230                 235                 240

Leu Thr Asn Gln Lys Gly Glu Asp Ala Trp Pro Ile Thr Ser Thr Thr
                245                 250                 255

Phe Ile Leu Ile His Lys Asp Gln Lys Lys Pro Glu Gln Gly Thr Glu
            260                 265                 270

Val Leu Lys Phe Phe Asp Trp Ala Tyr Lys Thr Gly Ala Lys Gln Ala
        275                 280                 285

Asn Asp Leu Asp Tyr Ala Ser Leu Pro Asp Ser Val Val Glu Gln Val
290                 295                 300

Arg Ala Ala Trp Lys Thr Asn Ile Lys Asp Ser Ser Gly Lys Pro Leu
305                 310                 315                 320

Tyr

<210> SEQ ID NO 3
<211> LENGTH: 10
<212> TYPE: PRT
<213> ORGANISM: Homo sapiens

<400> SEQUENCE: 3

Glu Gln Lys Leu Ile Ser Glu Glu Asp Leu
 1               5                  10
```

```
<210> SEQ ID NO 4
<211> LENGTH: 9
<212> TYPE: PRT
<213> ORGANISM: Influenza virus

<400> SEQUENCE: 4

Tyr Pro Tyr Asp Val Pro Asp Tyr Ala
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 5

His His His His His His
 1               5
```

SENSOR PROTEINS AND ASSAY METHODS

RELATED APPLICATIONS

This application is a continuation of U.S. application Ser. No. 11/837,180, filed Aug. 10, 2007 now abandoned which claims the benefit under 35 U.S.C. 119(e) of U.S. Provisional Patent Application No. 60/822,206, filed Aug. 11, 2006, the entire disclosure of each of which is incorporated herein by reference.

1. FIELD OF THE INVENTION

The present invention, in part, provides compositions and methods related to molecular detection including assays for the detection of molecules. The invention also includes reactions, methods and assays coupled to molecular detection assays. The invention also provides, in part, reagents for detecting conformational changes in a ligand binding molecule (e.g., a protein) upon binding a molecule.

2. BACKGROUND OF THE INVENTION

Biosensors are analytical tools that can be used to measure the presence of a molecular species in a sample by combining the molecular recognition properties of biological macromolecules with signal transduction mechanisms that couple ligand binding to readily detectable physical changes. Commonly, a biosensor combines a naturally occurring macromolecule (e.g., an enzyme or an antibody), with the generation of a suitable physical signal particular to the molecule in question.

*Escherichia coli* periplasmic binding proteins are members of a protein superfamily (bacterial periplasmic binding proteins) that has been shown to be suited for the engineering of biosensors (e.g., see, U.S. Pat. Nos. 5,898,069 and 6,277,627). Bacterial periplasmic binding proteins typically comprise two domains linked by a hinge region (Quiocho & Ledvina, Molec. Microbiol. 20:17-25, 1996). The ligand-binding site is typically located at the interface between the two domains. The proteins typically adopt two conformations: a ligand-free open form, and a ligand-bound closed form, which interconvert via a hinge-bending mechanism upon ligand binding. This global, ligand mediated conformational change can be exploited to couple ligand binding to changes in fluorescence intensity by positioning single fluorophores in locations that undergo conformational changes in concert with the global change (e.g., Brune et al., Biochemistry 33:8262-8271, 1994; Gilardi et al., Prot. Eng. 10:479-486, 1997; Gilardi et al., Anal. Chem. 66:3840-3847, 1994; Marvin et al., Proc. Natl. Acad. Sci. USA 94:4366-4371, 1997, Marvin and Hellinga, J. Am. Chem. Soc. 120:7-11, 1998; Tolosa et al., Anal. Biochem. 267:114-120, 1999; Dattelbaum & Lakowicz, Anal. Biochem. 291:89-95, 2001; Marvin & Hellinga, Proc. Natl. Acad. Sci. USA 98:4955 4960, 2001; Salins et al., Anal. Biochem. 294:19-26, 2001).

In biological systems, changes in phosphorylation state and fluctuations in the concentration of inorganic phosphate are associated with a number of important events. Because inorganic phosphate (Pi) is involved in a number of important biological processes, it is often desirable to be able to measure the concentration of Pi and changes in such concentration in biological systems. Phosphate assays, which measure Pi concentration, are useful in a number of diagnostic methods, as well as in research related to the functioning of biological systems.

A number of diseases and conditions present with elevated or depressed levels of serum inorganic phosphate concentration. Moreover, the major energy requirements of the body are fulfilled by deriving energy from alterations in the phosphorylation state of nucleotides. A large number of enzymes of importance to drug discovery consume or produce inorganic phosphate (Pi), either directly or through coupled reactions. These enzymes include protein and lipid phosphatases, ATPases, drug transporters, GTPases, phosphorylases, phosphodiesterases, and prenyl transferases. Additional applications include monitoring of phosphate in clinical samples and in process control within the bioproduction industry. The current standard assay for phosphate quantitation is an absorbance assay based on malachite green, which is sensitive to about 5 $\mu$M phosphate, and robust at ~25 $\mu$M phosphate. In addition to limited sensitivity, this assay suffers in that it is absorbance-based, and thus is far from ideal for high throughput screening. A third disadvantage is that malachite green can only be used in an end-point format, precluding kinetic analysis that could be useful for lead characterization and optimization of small molecules. It is desirable to utilize phosphate assays having a rapid response rate, in order to monitor the kinetics of biological and chemical processes which involve the production or consumption of Pi.

Phosphodiesterases cleave phosphodiesters to phosphomonoesters Important classes of phosphodiesterases include those that act upon cyclic nucleotide phosphodiesters (cAMP or cGMP). Present methods to quantitate such activity depend on binding of either the substrate (cNMP) or product (NMP) to a binding partner (an antibody or other reagent) which can be detected by displacement of a fluorescent moiety from that binding partner. Such binding partners can be expensive and can show poor specificity between substrate and product, limiting assay performance. Methods that depend on detecting a decrease in the amount of substrate present are problematic in that low levels of enzyme activity can be difficult to detect. Methods which are part of the invention, described herein, do not suffer from these disadvantages.

Fluorescent and radiometric methods exist to detect kinase activity. However, very few truly "generic" methods exist that can be applied to assay a wide range of kinases. Many kinase assays depend on the use of antibodies that detect specific phosphorylated residues in a substrate, or on the phosphorylation of specific peptide substrates (that may not be optimal for the kinase being assayed). Methods which are part of the invention, described herein, can be used with "native" kinase substrates, do not depend on the use of radioactivity or antibodies, and detect formation of product rather than a decrease in substrate.

There is a broad demand for phosphate detection reagents and assays. These include, for example, both basic and applied biochemists, in pharmaceuticals and academia, as well as high throughput screening facilities. One need among researchers is for sensitive, but also kinetic assays for enzymatic activities. One need among HTS facilities is for sensitive, robust, and miniaturizable assays, preferably, but not necessarily, resistant to compound interference.

Citation or discussion of a reference herein is not to be construed as an admission that such is prior art to the present invention.

SUMMARY OF THE INVENTION

The present invention relates, in part, to ligand-binding molecules (e.g., a protein) labeled with a pair of moieties suitable for resonance energy transfer (RET) measurements (e.g., time resolved fluorescence resonance energy transfer (TR-FRET), fluorescence resonance energy transfer (FRET) and luminescence resonance energy transfer (LRET)). A pair of moieties can be covalently attached or non-covalently attached (e.g., via antibody binding) to the ligand-binding molecule. In some cases, one of the moieties is covalently attached and the other is non-covalently attached.

The invention relates, in part, to assay methods based upon one or more of the following principles: (a) detection of a conformational change in a ligand binding molecule; or (b) detection of an end product or intermediate of a reaction.

The ligand binding molecule can essentially be any molecule that binds a ligand, undergoes a conformational change upon binding and/or release of a ligand and can be labeled directly and or indirectly with detectable moieties, wherein a detectable signal changes upon binding and/or release of the ligand. Ligand binding molecules of the invention include, but are not limited to, proteins, peptides, nucleic acids (e.g., RNA, DNA and the like) and polymers (e.g., natural or non-natural polymers In some embodiments, the ligand-binding molecule is a Periplasmic Binding Protein (such as phosphate binding protein (PBP)), which are a family of prokaryotic proteins which bind specific ligands, such as phosphate, iron, sulfate, glutamate, or one of many other small molecules. These proteins typically consist of two domains linked by a hinge region (Quiocho and Ledvina 1996). The ligand-binding site is typically located at the interface between the two domains. Periplasmic Binding Proteins typically adopt two conformations: a ligand-free open form and a liganded closed form, which interconvert via a hinge-bending mechanism upon ligand binding. In some embodiments, the ligand-binding molecule is a human plasma phosphate binding protein (HPBP). See, e.g., Morales et al. *Structure, Vol* 14, 601-609, March 2006.

TR-FRET measurements are sensitive to the distance between the donor and acceptor moieties, the orientation of the donor and acceptor moieties and/or due to a change in the environment of one of the fluorophores. For example, conformational changes in a protein labeled with both donor and acceptor moieties can lead to a change in TR-FRET. Such conformational changes occur in many compounds (e.g., proteins) upon ligand binding. Acceptor moieties can be chemically attached (e.g., to amines or thiols), genetically encoded (e.g., fusion to a fluorescent protein), or noncovalently attached (e.g., with an antibody, streptavidin, or other binding-protein). Donor moieties (e.g., Tb-chelate) can be attached to the protein chemically (e.g., via amines or thiols), genetically encoded (e.g., fusion to a fluorescent protein) or associated noncovalently (e.g., with a fluorescently labeled antibody, streptavidin, or other binding-protein). A PBP could be produced recombinantly and purified, purified from native sources, or not purified (e.g., from a cell lysate).

In some embodiments, the present invention provides compositions and methods for the detection and quantification of phosphate (e.g., inorganic phosphate), iron, sulfate, glutamate, and/or a small molecule, especially in biological solutions. In some embodiments of the invention a ligand binding molecule is a maltose binding protein, an arabinose binding protein, a dipeptide binding protein, a Glu/Asp BP, a Fe(III) BP, a glucose binding protein, a histidine binding protein, a glutamine binding protein, a ribose binding protein, or a sulfate binding protein, e.g., see Lorimier et al. Protein Science, 2002, 11:2655-2675. In some embodiments, a ligand binding protein binds a monosaccharide (e.g., arabinose, glucose, and ribose), di- and trisaccharides of glucose (e.g., maltose), an amino acid (e.g., glutamate/aspartate, histidine, and glutamine), di- and tripeptides, an oxyanion (e.g., phosphate and sulfate), or a metal ion (e.g., Fe(III)). In some embodiments, a ligand binding molecule binds phosphate and arsenate but not other oxyanions. In some embodiments, a ligand binding molecule binds glucose and galactose but not other monosaccharides. In some embodiments of the invention, a ligand binding molecule binds ATP, NADPH, an amino acid, or a peptide. In some embodiments, the ligand is a peptide or protein from a prokaryote, a eukaryote, a mammal, a primate, a human, or a mouse.

In particular embodiments, the present invention relates to a modified phosphate binding protein and the use of such a protein in a phosphate assay. Other embodiments of the invention provide methods for measuring, detecting and/or monitoring ligand binding.

One embodiment of the present invention relates to a phosphate binding protein (PBP). In some embodiments, the PBP is modified to be capable of resonance energy transfer (RET). In some embodiments, there is a detectable difference between the RET of the unbound PBPs and the phosphate bound PBPs of the invention. Therefore, the modified PBPs of the invention are capable of acting as biosensors for phosphate (e.g., inorganic phosphate (Pi)). Modified PBPs of the invention can be used in various assays where the detection of phosphate is desired. Additionally, an assay involving phosphate (e.g., kinase reaction) can be coupled to another assay (e.g., involving phosphatase) that results in a change in phosphate concentration (e.g., increase or decrease), which can then be detected by the modified PBPs of the present invention. In one embodiment, the modified PBP is derived from an *E. coli* PBP, e.g., encoded by the *E. coli* phoS gene.

Other embodiments of the invention relate to a modified ligand binding molecule (e.g., a Periplasmic Binding Protein) that is capable of being used for the detection of iron, sulfate, glutamate, and/or a small molecule.

The present invention also provides general and specific modifications of a PBP or other ligand binding molecule. In some embodiments, a moiety that is a component of a RET pair (e.g., donor or acceptor moieties) can be attached to a ligand binding protein molecule (e.g., PBP) via a thiol linkage to a cysteine amino acid. In particular embodiments, at least one cysteine amino acid can be substituted or inserted into the amino acid sequence of the ligand binding protein molecule (e.g., PBP) to allow a component of a RET pair to be attached to the ligand binding protein molecule (e.g., PBP) via a thiol linkage to the inserted or substituted cysteine amino acid. In some embodiments, both the donor and acceptor moiety are attached to the ligand binding protein molecule (e.g., PBP) via a cysteine or thiol linkage.

In particular embodiments, a moiety that is a component of a RET pair (e.g., donor or acceptor moieties) can be attached to a ligand binding protein molecule (e.g., PBP) via an amine linkage to an amino acid (e.g., lysine) of the ligand binding protein molecule (e.g., PBP). In some embodiments, the donor or acceptor moiety is attached to the ligand binding protein molecule (e.g., PBP) via an amine linkage. In particular embodiments, both the donor and acceptor moiety are attached to the ligand binding protein molecule (e.g., PBP) via an amine linkage. In specific embodiments, the donor or acceptor moiety is attached to the PBP via an amine linkage and the other moiety is attached via a thiol linkage. In some embodiments, one of the components of a RET pair are randomly attached to the ligand binding protein molecule (e.g., PBP), for example via amine linkage.

One advantage of some of modified ligand binding molecules (e.g., a modified PBP) described herein is that the means of measurement is via RET (e.g., TR-RET or TR-FRET. These methods of detection are generally better for high throughput screening compared to existing assays. In general, TR-FRET assays are much less prone to interference from library compounds. Also, these assays can be ratiometric, which results in more precise data, and a more robust assay.

The present invention provides sensitive phosphate assays and enables the use of less enzyme and/or other reagents. In addition, the present invention allows for detailed kinetic analysis of enzymes, rather than only end point assays (e.g., as with malachite green). For high throughput assays, some embodiments of the invention lead to reduced costs by using more sensitive detection methods, e.g., because of the use of less enzyme and/or other reagents. Embodiments of the present invention also allow for more cost-effective screening and more meaningful screening data by eliminating or reducing compound interference. Furthermore, some formats described herein may enable the screening of new targets that were not deemed feasible with existing technologies.

In some embodiments, modified ligand binding molecules (e.g., modified PBPs) and methods of the invention allow, in part, related detection assays for phosphate, iron, sulfate, glutamate, and/or a small molecule to be miniaturized; allow, in part, for lower amounts of reagents to be consumed; and allow, in part, for more robust and higher quality data due to reduced compound interference, e.g., in the case of TR-FRET related assays.

Modified ligand binding molecules and methods of the invention can be utilized in a variety of ways including, but not limited to, assay development, high throughput screening (HTS), target identification, lead optimization, bioproduction, pre-clinical investigation, and kinetic/enzymatic analyses. Modified ligand binding molecules utilizing TR-FRET (e.g., utilizing a lanthanide metal complex as the donor moiety) are, in many instances, well suited for HTS, although non-TR-FRET versions of the modified ligand binding molecules (e.g., a modified PBP) of the invention can also be used for HTS. Modified ligand binding molecules (e.g., modified PBPs) of the present invention provide, in many instances, a simple solution to assay many different enzymes either directly or through coupled reactions.

One embodiment of the invention provides a ligand binding molecule (e.g., a phosphate binding protein) comprising a resonance energy transfer (RET) pair of moieties comprised of at least one donor moiety and at least one acceptor moiety, wherein the ligand binding molecule is capable of binding a ligand and wherein the binding results in a change in RET. One embodiment of the invention provides a phosphate binding protein comprising a RET pair of moieties comprised of at least one donor moiety and at least one acceptor moiety, wherein the phosphate binding protein is capable of binding a phosphate and wherein the binding results in a change in RET. In some embodiments, the RET increases upon binding the ligand. In some embodiments, the RET decreases upon binding the ligand. In some embodiments, the ligand is inorganic phosphate (Pi).

In some aspects of the invention, the change in RET is caused by a conformational change of the protein upon binding the phosphate. In some embodiments, the change in RET is caused by a conformational change of the ligand binding molecule upon releasing the ligand (e.g., phosphate). In some embodiments, the distance between the at least two moieties is altered upon binding and/or release the ligand (e.g., phosphate). In some embodiments, the orientation between the at least two moieties is altered upon binding and/or release of the ligand (e.g., phosphate).

In some aspects of the invention, the RET pair is capable of time resolved RET. In some embodiments of the invention, the at least one acceptor moiety is selected from the group consisting of a fluorescein, a rhodamine, a GFP, a GFP derivatives, a fluorescent protein, a FITC, a 5-carboxyfluorescein, a 6-carboxyfluorescein, a 7-hydroxycoumarin-3-carboxamide, a 6-chloro-7-hydroxycoumarin-3-carboxamide, a fluorescein-5-isothiocyanate, a dichlorotriazinylaminofluorescein, a tetramethylrhodamine-5-isothiocyanate, tetramethylrhodamine-6-isothiocyanate, a succinimidyl ester of 5-carboxyfluorescein, a succinimidyl ester of 6-carboxyfluorescein, a 5-carboxytetramethylrhodamine, a 6-carboxymethylrhodamine, a 7-amino-4-methylcoumarin-3-acetic acid, ALEXA FLUOR dye 488, ALEXA FLUOR dye 633, ALEXA FLUOR dye 647, 6-IAF, 5-IAF, BODIPY FL dye maleimide, BODIPY FL dye iodoacetamide, fluorescein-5-maleimide, OREGON GREEN dye 488iodoacetamide, OREGON GREEN dye 488 maleimide and 5-(bromomethyl)fluorescein. The acceptor moiety may also be a dye wherein the dye comprises a xanthene, a cyanine, an indole, a benzofuran, a coumarin, a borapolyazaindacine, or a semiconductor nanocrystal.

In some embodiments, a donor moiety comprises a luminescent metal complex. In some aspects of the invention, a luminescent metal complex comprises an organic antenna moiety, a metal liganding moiety and a lanthanide metal ion. In some embodiments, the metal complex is a lanthanide metal complex. In some aspects of the invention, a lanthanide metal complex comprises an organic antenna moiety, a metal liganding moiety and a lanthanide metal ion. In some embodiments, the lanthanide metal ion is selected from the group consisting of: Sm(III), Ru(III), Eu(III), Gd(III), Tb(III), and Dy(III). In some embodiments, the lanthanide ion is a Europium ion or a Terbium ion. In some aspects of the invention, the organic antenna moiety is selected from the group consisting of: rhodamine 560, fluorescein 575, fluorescein 590, 2-quinolone, 4-quinolone, 4-trifluoromethylcoumarin (TFC), 7-diethyl-amino-coumarin-3-carbohydrazide, 7-amino-4-methyl-2-coumarin (carbostyril 124), 7-amino-4-methyl-2-coumarin (coumarin 120), 7-amino-4-trifluoromethyl-2-coumarin (coumarin 124), and aminomethyltrimethylpsoralen. In some embodiments of the invention, the metal liganding moiety is a metal chelating moiety selected from the group consisting of: EDTA, DTPA, TTHA, DOTA, NTA, HDTA, DTPP, EDTP, HDTP, NTP, DOTP, DO3A, DOTAGA, and NOTA. In some aspects of the invention, the lanthanide metal complex has a structure: -$L_n$-A-$S_n$-$C_M$, or -$L_n$-$C_M$-$S_n$-A, wherein A represents an organic antenna moiety; L represents a linker; S represents a spacer; n can be 0 or 1; C represents a metal chelating moiety; and M represents a lanthanide metal ion coordinated to C. In some embodiments, a luminescent metal complex comprises CS124-DTPA-Phe-NCS-Tb or CS 124-DTPA-EMCH-Tb.

In some aspects of the invention, a ligand binding molecule (e.g., a PBP) comprises at least one non-native cysteine amino acid. In some embodiments, a first or second moiety is attached to a non-native cysteine amino acid. In some embodiments of the invention, the protein comprises at least two non-native cysteine amino acids. In some embodiments, a first and second moieties are attached to the non-native cysteine amino acids. In some aspects of the invention, at least one non-native cysteine amino acid is introduced by substituting or inserting the at least one cysteine amino acid into a ligand binding molecule.

In some aspects of the invention, the ligand binding molecule is derived from and/or comprises a PBP. In some embodiments, the amino acid sequence of the PBP is derived from the phoS gene. In some embodiments, the amino acid sequence encoded by the phoS gene is SEQ ID NO:1 or SEQ ID NO:2. In some aspects of the invention, the phosphate binding protein comprises an amino acid sequence 90% homologous to SEQ ID NO:1 or SEQ ID NO:2. In some embodiments of the invention, the ligand binding molecule derived from and/or comprising a PBP further comprises at least one non-native cysteine amino acid. In some aspects of the invention, a PBP comprises an amino acid substitution selected from the group consisting of A47C, A197C, Q201C and E268C. In some embodiments, the PBP comprises at least two non-native cysteine amino acids. In some embodiments, the PBP comprising at least two non-native cysteine amino acids comprises an amino acid substitution selected from the group consisting of A47C, A197C, Q201C and E268C. In some aspects of the invention, a PBP comprises at least 2 amino acid substitutions selected from the group consisting of A197C/E268C, A47C/A197C, A47C/E268C, Q201C/E268C, A47C/Q201C and A197C/Q201C. In some embodiments, a first and/or second moiety is attached to a non-native cysteine amino acid.

In some aspects of the invention, an at least one donor moiety and/or acceptor moiety is linked to the phosphate binding protein via an amine or thiol linkage.

The invention also provides a method of measuring phosphate in a first sample comprising: (a) contacting the first sample with a ligand binding molecule of the invention comprising at least one donor moiety and at least one acceptor moiety that are capable of RET; (b) exposing (a) to a wavelength of light that excites the donor moiety of the RET pair; and (c) measuring the emission from the acceptor moiety of the RET pair and/or measuring the emission from the donor moiety of the RET pair. In some aspects, the method comprises calculating a ratio between the emission of the donor and acceptor moieties of the RET pair. In some embodiments of the invention, the method further comprises: (i) contacting a second sample with a ligand binding molecule of the invention comprising at least one donor moiety and at least one acceptor moiety that are capable of RET, wherein the second sample comprises a known amount of the ligand (e.g., phosphate); (ii) exposing (i) to a wavelength of light that excites the donor moiety of the RET pair; and (iii) measuring the emission from the acceptor moiety of the RET pair and/or measuring the emission from the donor moiety of the RET pair in (ii). In some embodiments, the method comprises calculating a ratio between the emission of the donor and acceptor moieties of the RET pair in (ii). In some embodiments, the method comprises: (i) separately contacting multiple samples with a ligand binding molecule of the invention (e.g., a PBP), wherein the multiple samples comprise a known amount of the ligand (e.g., phosphate); (ii) exposing (i) to a wavelength of light that excites the donor moiety of the RET pair; and (iii) measuring the emission from the acceptor moiety of the RET pair in each sample and/or measuring the emission from the donor moiety of the RET pair in (iii). In some embodiments, the method comprises calculating a ratio between the emission of the donor and acceptor moieties of the RET pair in (iii). The methods of the invention also provide measuring the emission at multiple time points. In some embodiments of the invention, the amount of ligand (e.g., phosphate) in the first sample is determined by comparing the emission from the samples, e.g., comparing the emission from the first sample to the multiple samples.

In some embodiments, the donor moiety is not a GFP. In some embodiments, the donor moiety is not an aequorin protein. In some embodiments, the donor moiety is not a protein. In some embodiments, the acceptor moiety is not a GFP. In some embodiments, the acceptor moiety is not an aequorin protein. In some embodiments, the acceptor moiety is not a protein.

4. BRIEF DESCRIPTION OF THE FIGURES

For the purpose of illustrating the invention, there are depicted in the drawings certain embodiments on the invention. However, the invention is not limited to the precise arrangements and instrumentalities of the embodiments depicted in the drawings.

Figure 10A:
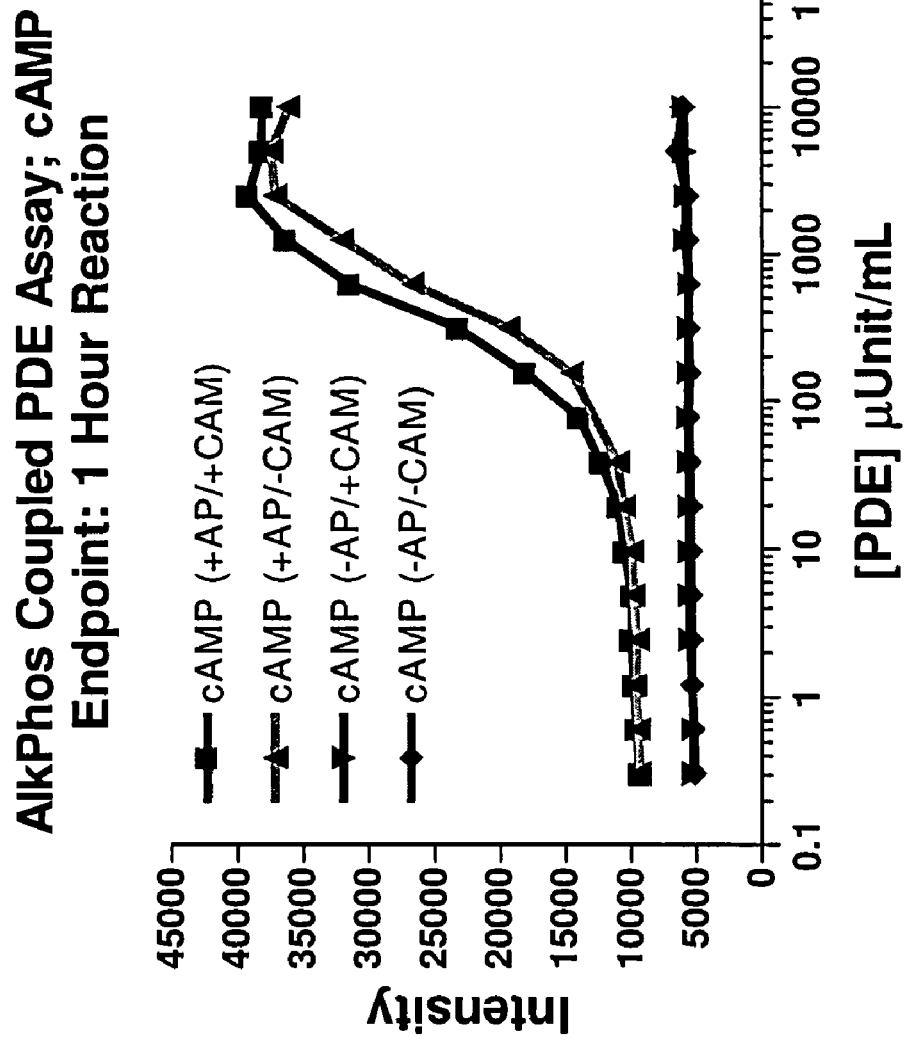
Figure 10B:
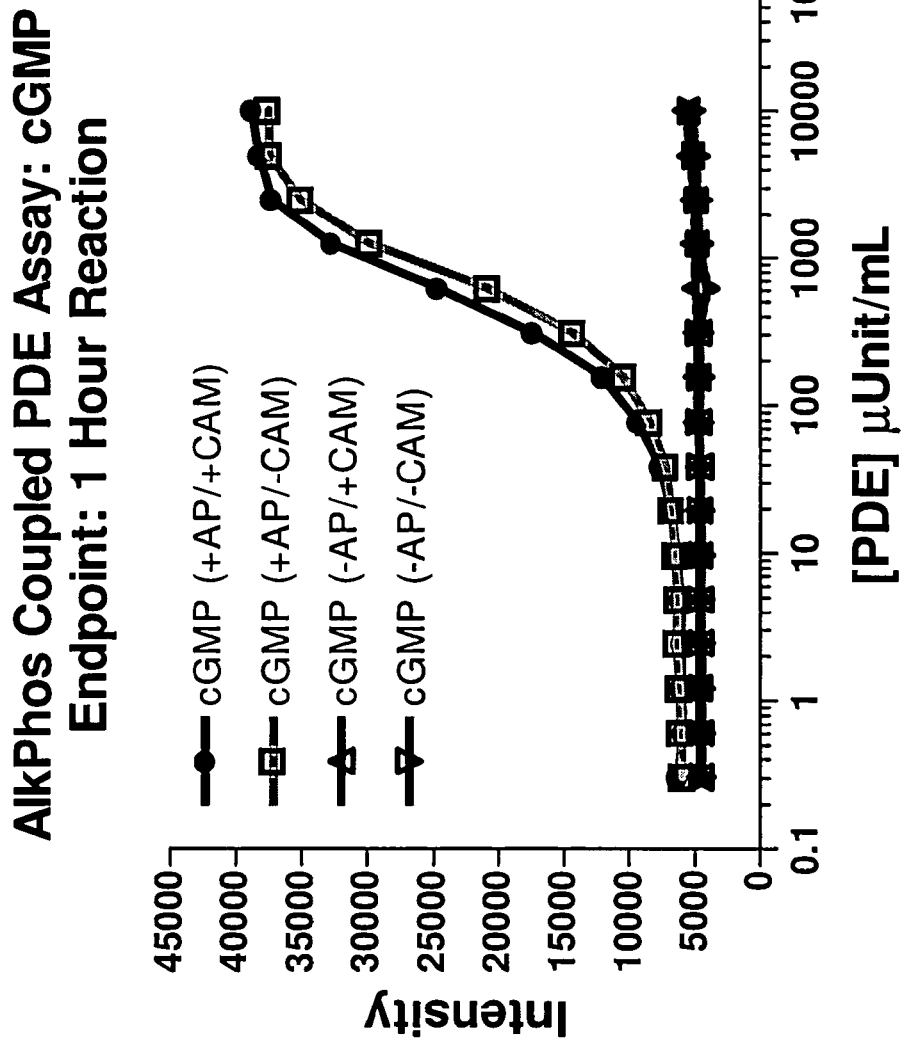

FIG. 10 shows a titration of calmodulin-sensitive phosphodiesterase from bovine brain that is incubated with 100 uM cAMP (FIGS. 10A) or cGMP (FIGS. 10B) in the presence of 1 uM coumarin-PBP sensor, 10 uM $Ca^{2+}$, with or without 1 unit/mL alkaline phosphatase and 1 unit/mL calmodulin. Experimental procedures are described in Example 6.4.

Figure 11:
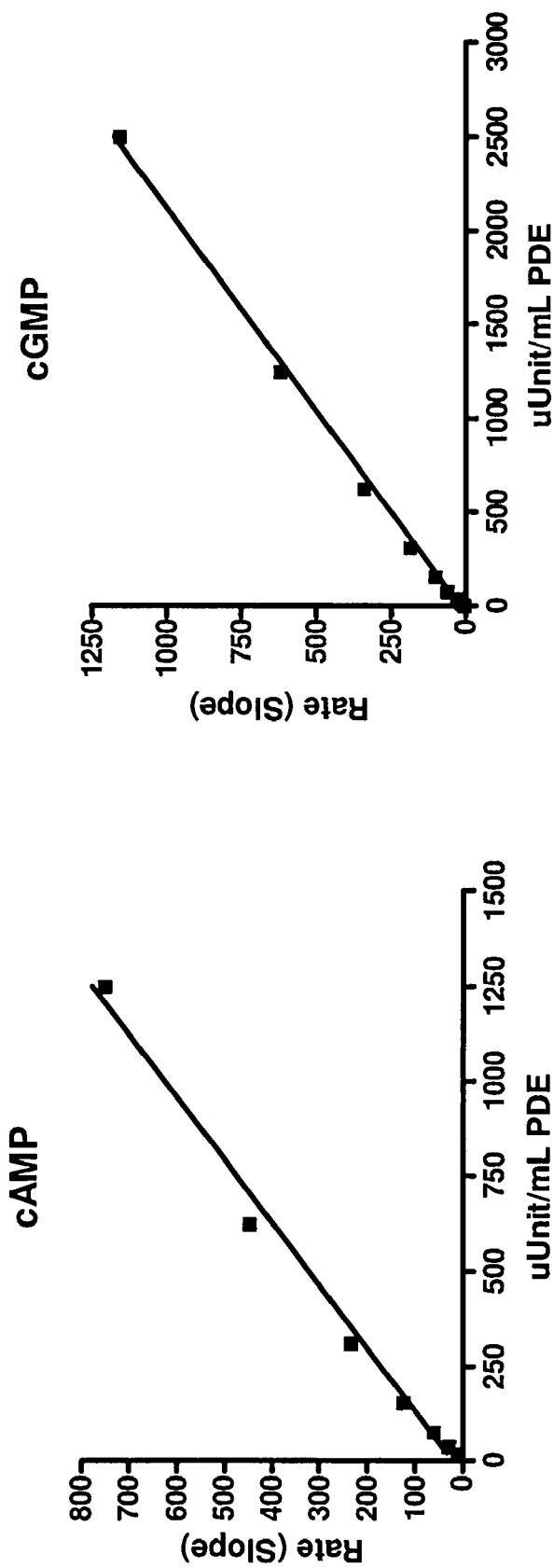

FIG. 11 shows an example of a phosphodiesterase assay coupled reaction performed in "kinetic mode". Experimental procedures are described in Example 6.4

Figure 12:
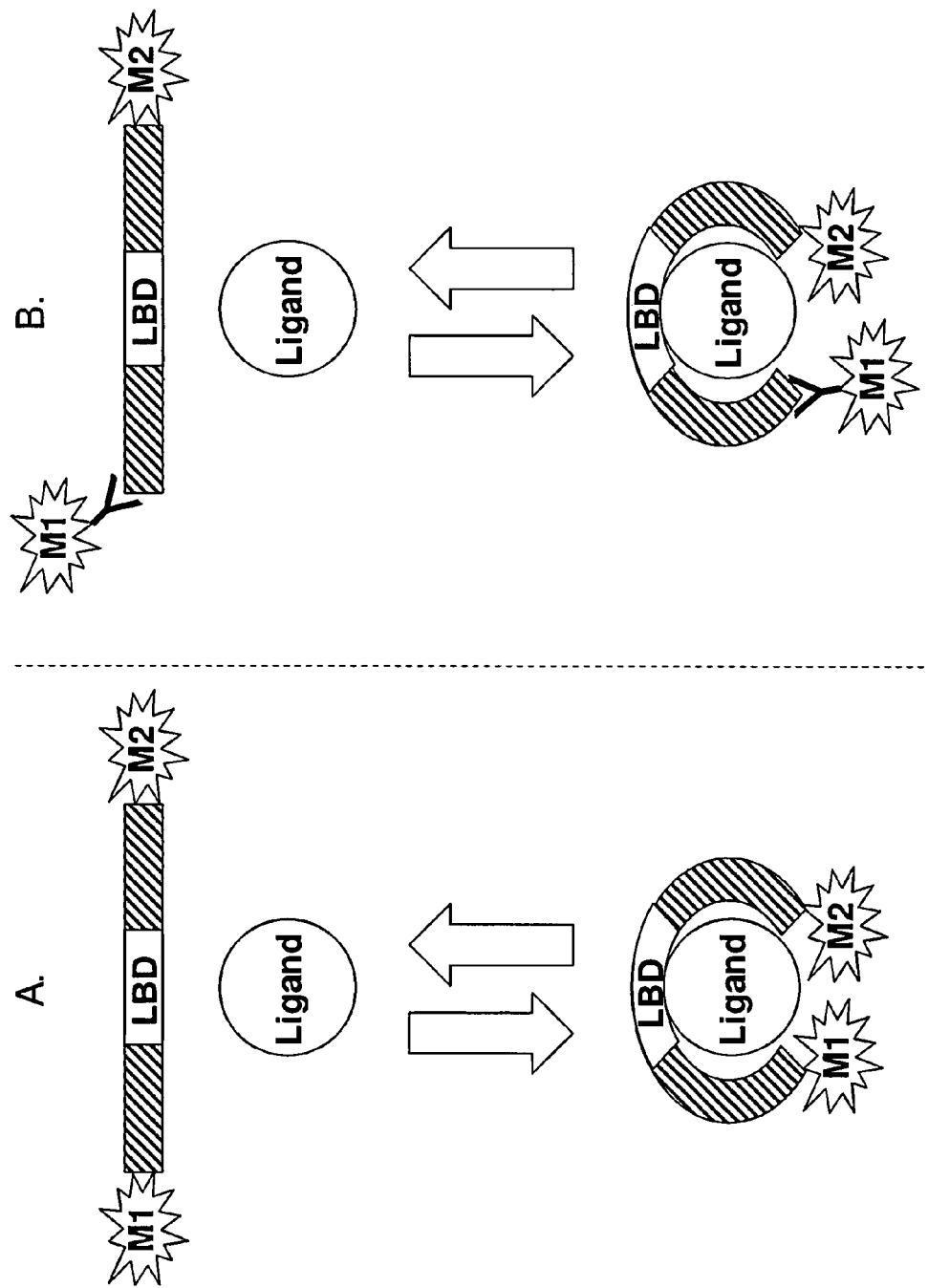

FIG. 12 is one representation of the present invention. LBD=Ligand binding domain. M1 and M2 represent moiety 1 and moiety 2 respectively. FIG. 12A depicts both of the moieties are directly attached to the ligand binding molecule. FIG. 12B depicts M1 as bound to the ligand binding molecule via a binding partner (e.g., an antibody). Another embodiment of the invention, not shown here provides both of the moieties being bound via binding partners.

Figure 13:
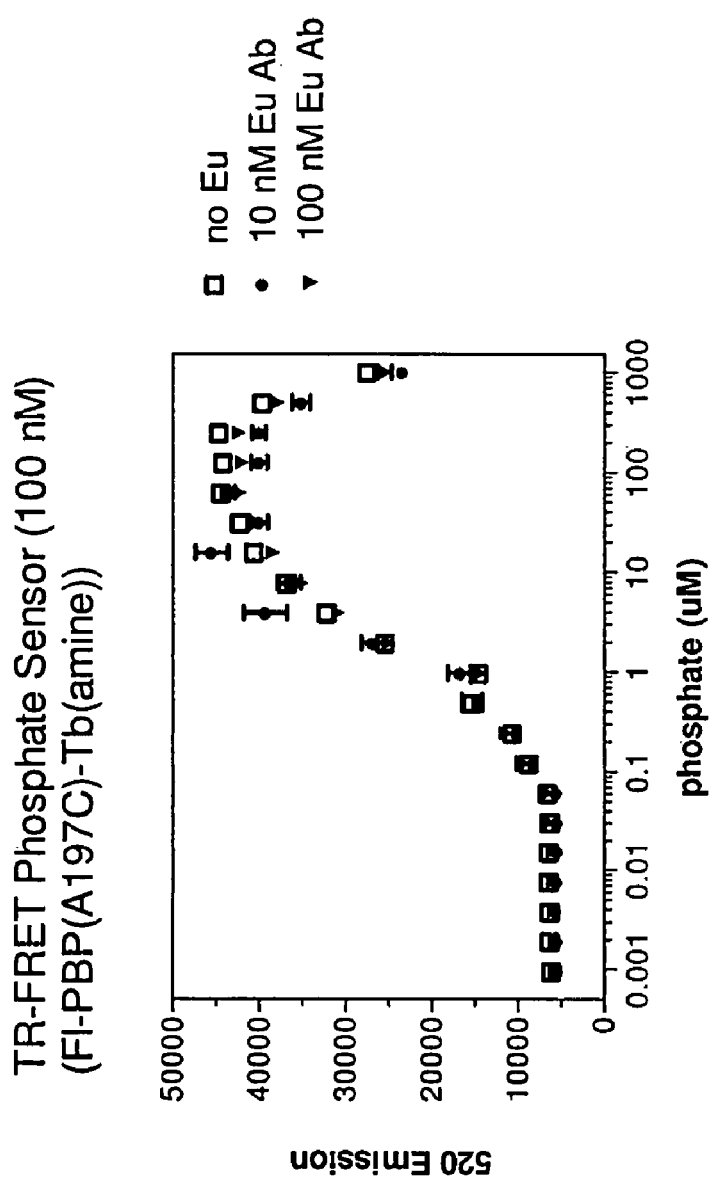

FIG. 13 shows results of an assay with Fl-PBP-Tb and measuring emission at 520 nm Experimental procedures are described in Example 9.

Figure 14:
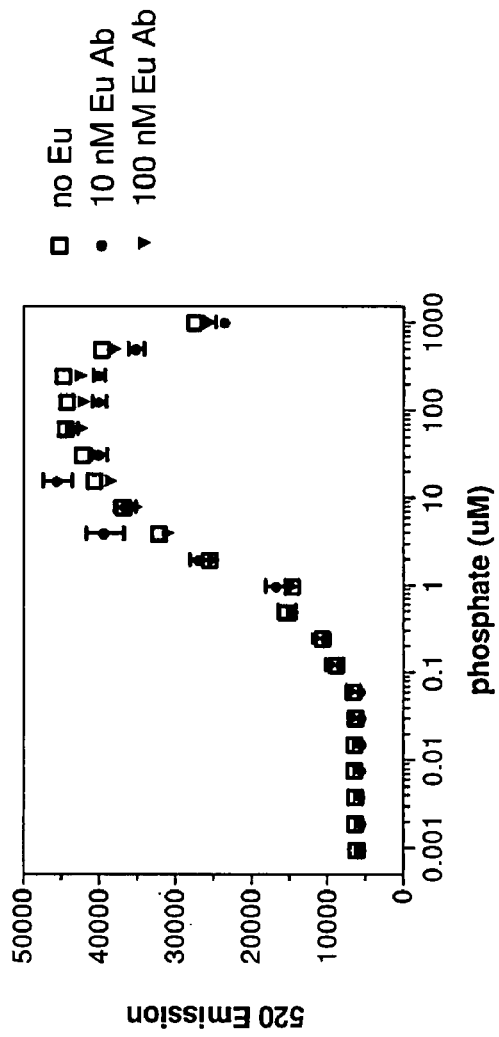

FIG. 14 shows results of an assay with Fl-PBP-Tb and measuring the ratio of emission at 520 nm to 615 nm. Experimental procedures are described in Example 9.

Figure 15:
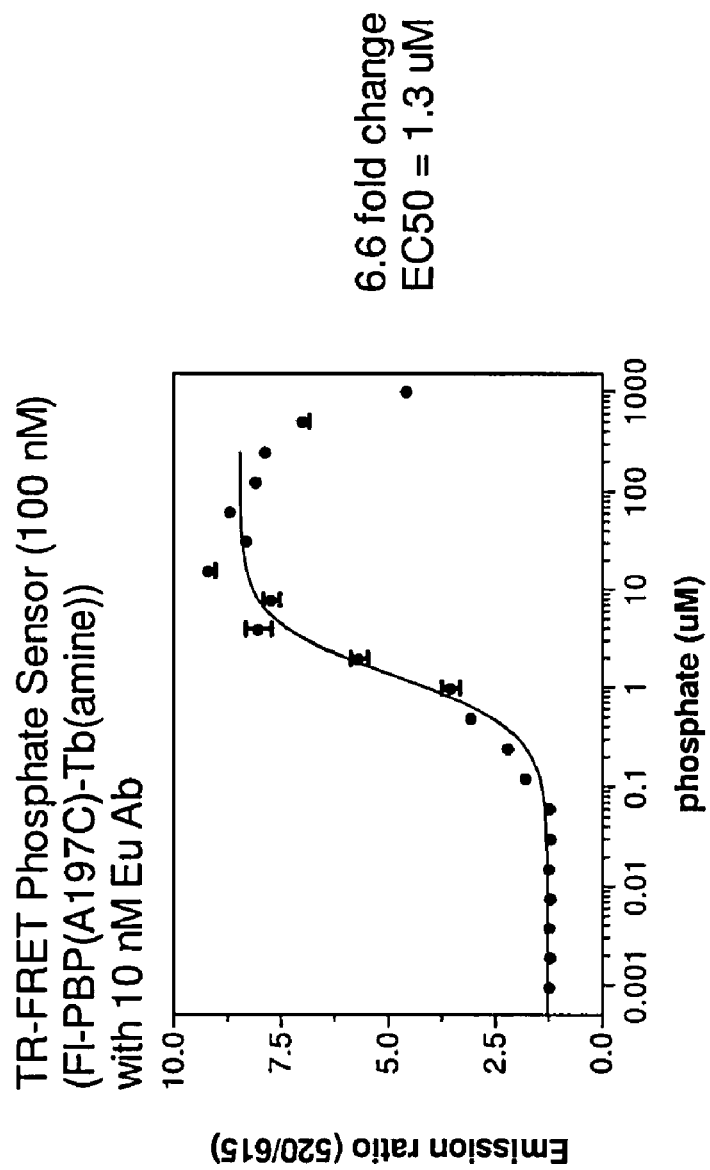

FIG. 15 shows results of an assay with Fl-PBP-Tb and measuring the ratio of emission at 520 nm to 615 nm. Experimental procedures are described in Example 9.

5. BRIEF DESCRIPTION OF THE SEQUENCES

SEQ ID NO:1 is an amino acid sequence of an *E. coli* phosphate binding protein (phoS). This sequence includes a signal sequence, which is underlined. (GenBank Accession No. AAA24378)

MKVMRTTVATVVAATLSMSAFSVFAEASLTGAGATFPAPVYAKWADTYQK

ETGNKVNYQGIGSSGGVKQIIANTVDFGASDAPLSDEKLAQEGLFQFPTV

IGGVVLAVNIPGLKSGELVLDGKTLGDIYLGKIKKWDDEAIAKLNPGLKL

PSQNIAVVRRADGSGTSFVFTSYLAKVNEEWKNNVGTGSTVKWPIGLGGK

GNDGIAAFVQRLPGAIGYVEYAYAKQNNLAYTKLISADGKPVSPTEENFA

NAAKGADWSKTFAQDLTNQKGEDAWPITSTTFILIHKDQKKPEQGTEVLK

FFDWAYKTGAKQANDLDYASLPDSVVEQVRAAWKTNIKDSSGKPLY

SEQ ID NO:2 an amino acid sequence of an *E. coli* phosphate binding protein (phoS), which does not include the signal sequence.

EASLTGAGATFPAPVYAKWADTYQKETGNKVNYQGIGSSGGVKQIIANTV

DFGASDAPLSDEKLAQEGLFQFPTVIGGVVLAVNIPGLKSGELVLDGKTL

GDIYLGKIKKWDDEAIAKLNPGLKLPSQNIAVVRRADGSGTSFVFTSYLA

KVNEEWKNNVGTGSTVKWPIGLGGKGNDGIAAFVQRLPGAIGYVEYAYAK

QNNLAYTKLISADGKPVSPTEENFANAAKGADWSKTFAQDLTNQKGEDAW

PITSTTFILIHKDQKKPEQGTEVLKFFDWAYKTGAKQANDLDYASLPDSV

VEQVRAAWKTNIKDSSGKPLY

6. DETAILED DESCRIPTION

Generally, the nomenclature used herein and many of the fluorescence, luminescence, computer, detection, chemistry, and laboratory procedures described herein are commonly employed in the art. Standard techniques are generally used for chemical synthesis, fluorescence or luminescence monitoring and detection, optics, molecular biology, and computer software and integration. Chemical reactions, cell assays, and enzymatic reactions are typically performed according to the manufacturer's specifications where appropriate. See, generally, Lakowicz, J. R. Topics in Fluorescence Spectroscopy, (3 volumes) New York: Plenum Press (1991), and Lakowicz, J. R. Emerging applications of florescence spectroscopy to cellular imaging: lifetime imaging, metal-ligand probes, multi photon excitation and light quenching, Scanning Microsc. Suppl. Vol. 10 (1996) pages 213-24, for fluorescence techniques; Sambrook et al., Molecular Cloning: A Laboratory Manual, 2ed. (1989) Cold Spring Harbor Laboratory Press, Cold Spring Harbor, N.Y., for molecular biology methods; Cells: A Laboratory Manual, 1st edition (1998) Cold Spring Harbor Laboratory Press, Cold Spring Harbor, N.Y., for cell biology methods; and Optics Guide Melles Griot® Irvine Calif., and Optical Waveguide Theory, Snyder & Love (published by Chapman & Hall) for general optical methods, all of which are incorporated herein by reference.

General methods for performing a variety of fluorescent or luminescent assays on luminescent materials are known in the art and are described in, e.g., Lakowicz, J. R., Topics in Fluorescence Spectroscopy, volumes 1 to 3, New York: Plenum Press (1991); Herman, B., Resonance Energy Transfer Microscopy, in Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361; and Bernard Valeur, "Molecular Fluorescence: Principles and Applications" Wiley VCH, 2002. Guidance in the selection and use of specific resonance acceptor moieties is available at, for example, Berlman, I. B., Energy transfer parameters of aromatic compounds, Academic Press, New York and London (1973), which contains tables of spectral overlap integrals for the selection of resonance energy transfer pairs. Additional information sources include the Molecular Probes Catalog (2003) and website; Invitrogen New Products Catalog (2006); Full Invitrogen Catalog (2005); Invitrogen Drug Discovery Solutions Catalog (2004); Invitrogen's website; and Tsien et al., 1990 Handbook of Biological Confocal Microscopy, pp. 169-178. Instruments useful for performing FP and/or RET and TR-RET applications are available from Tecan Group Ltd. (Switzerland) (Ultra, Ultra 384, Ultra Evolution); Perkin-Elmer (Boston, Mass.) (Fusion, EnVision, Victor V, and ViewLux), Amersham Bioscience (Piscataway, N.J.) (LeadSeeker); and Molecular Devices Corporation (Sunnyvale, Calif.) (Analyst AD, GT, and HT).

The term "RET" stands for resonance energy transfer, and refers to the transmission (e.g., radiationless) of an energy quantum from its site of absorption (the donor) to the site of its utilization (the acceptor) in a molecule, or system of molecules, by resonance interaction between donor and acceptor species, over distances considerably greater than interatomic. A donor is a moiety that initially absorbs energy (e.g., optical energy or electronic energy). A luminescent metal complex, as described herein, can comprise two donors: 1) an organic antenna moiety, which absorbs optical energy (e.g., from a photon); and 2) a lanthanide metal ion, which absorbs electronic energy (e.g., transferred from an organic antenna moiety). RET is sometimes referred to as fluorescent resonance energy transfer or Forster resonance energy transfer (both abbreviated FRET). RET includes TR-FRET, FRET and LRET. LRET uses the term "luminescence" which is more general than the term "fluorescence" (as in FRET).

The term "energy transfer pair" or RET pair as used herein refers to any two moieties that participate in energy transfer. In some embodiments, one of the moieties acts as a fluorescent reporter, e.g., a donor, and the other acts as an acceptor, which may be a quenching compound or a compound that absorbs and re-emits energy in the form of a detectable signal, e.g., a fluorescent signal ("Fluorescence resonance energy transfer." Selvin P. (1995) Methods Enzymol 246:300-334; dos Remedios C. G. (1995) J. Struct. Biol. 115:175-185; "Resonance energy transfer: methods and applications." Wu P. and Brand L. (1994) Anal Biochem 218:1-13). RET is a distance-dependent and/or orientation-dependent interaction between two moieties in which excitation energy, (e.g., light) is transferred from a donor to an acceptor without emission of a photon. Deuschle et al. (Protein Sci. 2005 14: 2304-2314) and Smith et al. (Protein Science, 2005, 14:64-73) describes how the distance between the RET pair and their orientation affect RET.

The acceptor may be fluorescent and emit the transferred energy at a longer wavelength, or it may be non-fluorescent, e.g., serves to diminish the detectable fluorescence of the reporter molecule (quenching). RET may be either an intermolecular or intramolecular event, and is typically dependent on the inverse sixth power of the separation of the donor and acceptor, making it useful over distances comparable with the dimensions of biological macromolecules. Thus, the spectral properties of the energy transfer pair as a whole, change in some measurable way if the distance and/or orientation between the moieties is altered. Self-quenching probes incorporating fluorescent donor-non-fluorescent acceptor combinations have been developed for detection of proteolysis (Matayoshi, (1990) Science 247:954-958) and nucleic acid hybridization ("Detection of Energy Transfer and Fluorescence Quenching" Morrison, L., in Nonisotopic DNA Probe Techniques, L. Kricka, Ed., Academic Press, San Diego, (1992) pp. 31 1-352; Tyagi S. (1998) Nat. Biotechnol. 16:49-53; Tyagi S. (1996) Nat. 14(8):947-8).

The term "acceptor" or "acceptor moiety" refers to a chemical or biological moiety that accepts energy via RET. In RET applications, acceptors may re-emit energy transferred from a donor moiety (e.g., fluorescent or luminescent moiety), for example as fluorescence. In some embodiments, the transfer is via RET or TR-RET. As used herein, a donor moiety (e.g., fluorescent or luminescent moiety) and an acceptor moiety (e.g., fluorescent moiety) are referred to as a "RET pair." Examples of acceptors include coumarins and related fluorophores; xanthenes such as fluoresceins and fluorescein derivatives; fluorescent proteins such as GFP and GFP derivatives; rhodols, rhodamines, and derivatives thereof; resorufins; cyanines; difluoroboradiazaindacenes; and phthalocyanines. Acceptors, including fluorescent acceptor moieties, can also be useful as fluorescent probes in FP assays. In most applications, the donor and acceptor dyes are different, in which case RET can be detected by the appearance of sensitized fluorescence of the acceptor or by quenching of donor fluorescence.

Ligand Binding Molecules

A ligand binding molecule used in the present invention can essentially be any molecule that binds a ligand, undergoes a conformational change upon binding and/or release of the ligand and can be labeled directly and or indirectly with detectable moieties, wherein the detectable signal changes upon the binding and/or release of the ligand. Ligand binding molecules of the invention include proteins, peptides, and nucleic acids (e.g., RNA, DNA, polymers (e.g., unnatural polymers) and the like).

Figure 2:
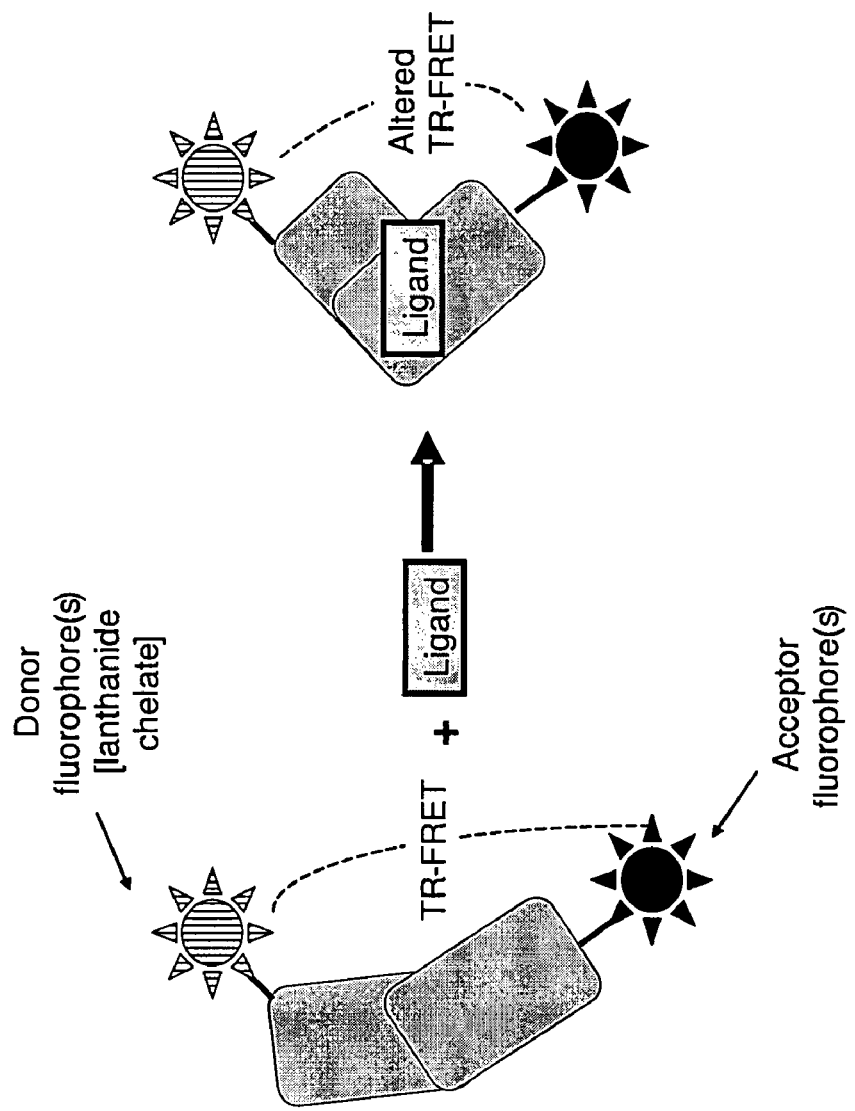
FIG. 2 is a graphical representation of a ligand binding molecule in a bound and unbound state. A ligand binding molecule is labeled with a RET pair of moieties and binding and/or release of the ligand causes a change in RET.

FIGS. 2 and 12 shows examples of some general principles for certain embodiments of the invention. In one embodiment, the ligand binding molecule is a nucleic acid. Nucleic acids are known to bind various molecules including, but not limited to proteins and other nucleic acids. In many instances, binding of a nucleic acid to a molecule causes the nucleic acid to undergo a conformational change. Various transcription factors and nucleic acid-binding proteins (e.g., DNA-binding proteins) can bind a nucleic acid resulting in a conformational change. The nucleic acid can be directly and/or indirectly labeled with detectable moieties, e.g., two moieties that comprise a RET pair. Many nucleic acid binding sites are known for numerous proteins. One skilled in the art can determine how and where to label a nucleic acid with at least two detectable moieties in order for there to be a change in a detectable signal upon binding and/or release of the bound molecule. For example, a nucleic acid sequence can be isolated or designed so that two domains of the nucleic acid bind a molecule. The nucleic acid labeled with two members of a FRET pair can be designed so that the two binding domains are brought within close proximity upon binding the ligand and in turn change the proximity of the members of the FRET pair, thereby changing detectable FRET.

The distance between the donor and acceptor of the RET (e.g., FRET) pair has a significant effect on the efficiency of RET (e.g., see Berney and Danuser, Biophysical Journal, (2003) 84:3992-4010 and Jares-Erijman and Jovin, Nature Biotechnology, (2003) 21(11):1387-1395). Although, the orientation of the donor and acceptor in relation to each other and their surrounding environment has been found to affect the efficiency of RET (Deuschle et al. Protein Sci. 2005 14: 2304-2314 and Smith et al. Protein Science, 2005, 14:64-73).

In some embodiments of the invention, the distance between the donor and acceptor moieties when bound and/or unbound to the ligand is between 0.1 nm and 100 nm, 1 nm and 10 nm, 1 nm and 5 nm, 5 nm and 10 nm, and 3 nm and 7 nm. In some instances, the distance between the members of the RET pair (e.g., the acceptor and donor moieties) is referred to as Forster distance (e.g., $R_o$).

In some embodiments of the invention, more than one acceptor and/or donor moiety are attached to the ligand binding molecule. In some embodiments, the ligand binding molecule is modified to be capable of FRET relay (e.g., see Watrob et al. 2003, Two-step FRET as a structural J. Am. Chem. Soc. 125: 7336-7343 and Smith et al. Protein Science, 2005, 14:64-73). In some embodiments, the ligand binding molecule is modified to be triply labeled, e.g., three fluorophores. In some embodiments, the ligand modified is labeled (e.g., covalently and/or non-covalently or a combination thereof) with 5-iodoacetamide fluoroscein (IAF), CY5 maleimide mono-reactive dye and tetramethylrhodamine-5-maleimide (TMR). This triple combination can be capable of FRET relay where excitation energy can be transferred from IAF to CY5 dye via TMR. In some embodiments, the FRET relay will demonstrate an increase in binding or release of a ligand by the ligand binding molecule. FRET relays can have utility in overcoming large distances (Watrob et al. 2003) and can provide large Stokes shifts.

Additionally, DNA binding proteins (DBP) can be modified to include (covalently or non-covalently) two members of a FRET pair, wherein upon DNA binding and/or release the modified DBP exhibits a detectable change in RET. These modified DBPs can be designed using methods and designs similar to those described herein, e.g. those described for modified PBPs.

Labels (e.g., donor and acceptor moieties) may be attached to ligand binding molecules by any conventional means known in the art. For example, a label may be attached via amines, carboxyl residues, thiol linkage on ligand binding molecules (e.g., modified ligand binding protein) and/or by antibody binding. In one embodiment, linkage of at least one label is via thiol groups on cysteine residues. In some embodiments, an antibody can provide one of the donor moieties and a ligand binding protein can provide the other. In some embodiments, one antibody can provide one of the donor moieties and another antibody can provide one of the acceptor moieties.

If appropriate, natural cysteine residues in the amino acid sequence of a ligand binding protein may be used for the attachment of the label. However, where no suitable natural cysteine residues are available for label attachment, cysteine residues may be engineered into the sequence of a ligand binding protein, e.g., by site-directed mutagenesis. Site-directed mutagenesis can be performed by methods well known in the art. For example, a coding sequence for a ligand binding protein is isolated and sequenced, and oligonucleotide probes are constructed to alter (e.g., by recombination) the codon encoding an amino acid which is desired to be changed into a codon encoding cysteine. The mutated gene is subsequently expressed, e.g., in a bacterial or eukaryotic expression system, to produce the mutated protein. In some embodiments, the label is attached to a cysteine residue on the protein via a linkage group which is thiol-reactive. Any thiol-reactive linkage group may be used. For example, an iodoacetamide linker may be used. In one embodiment, the linkage group comprises a maleimide linker.

In some embodiments, the cysteines are introduced by inserting a cysteine amino acid next to another amino acid. In some embodiments, the cysteines are introduced by substituting a cysteine amino acid in place of at least one other amino acid, i.e. substitution. Examples of specific substitutions are described herein wherein one amino acid is substituted with a cysteine amino acid. Embodiments of the invention also include substituting at least one cysteine amino acid in place of several adjacent amino acids, e.g., substituting for 2, 3, 4, 5, 6, 7, 8, 9, or 10 amino acids.

In some embodiments of the invention, RET increases upon binding or release of the ligand by a modified ligand binding molecule. In one embodiment, RET increases upon ligand binding. In some embodiments, this increase will be greater than 10%, greater than 20%, greater than 30%, greater than 40%, greater than 50%, greater than 60%, greater than 70%, greater than 80%, greater than 90%, greater than 100%, greater than 200%, greater than 300%, greater than 400%, greater than 750%, greater than 1000%, greater than 2000%, greater than 3000%, or greater than 5000%. In some embodiments, this change in RET is greater than 10% and less than 1000%, greater than 100% and less than 400%, greater than 20% and less than 200%, greater than 200% and less than 750%, greater than 400% and less than 1000%, greater than 750% and less than 3000%, or greater than 1000% and less than 5000%.

In one embodiment, RET decreases upon binding or release of the ligand by a modified ligand binding molecule. In some embodiments, this decrease will be greater than 10%, greater than 20%, greater than 30%, greater than 40%, greater than 50%, greater than 60%, greater than 70%, greater than 80%, or greater than 90%. In some embodiments, this change in RET is greater than 10% and less than 90%, greater than 20% and less than 60%, greater than 50% and less than 90%, or greater than 10% and less than 50%. In some embodiments, at least one member of the RET pair is attached in the vicinity of the binding cleft of a ligand binding molecule (e.g. *E. coli* PBP). In one embodiment, at least one member of the RET pair is attached within the binding cleft of a ligand binding molecule (e.g. *E. coli* PBP).

In some embodiments, FRET is the type of RET detected. In some embodiments, TR-FRET is the type of RET detected. In some embodiments, TR-RET is the type of RET detected.

Some embodiments of the invention can produce RET (e.g., FRET, TR-FRET, TR-RET or LRET) by any methods, for examples see, Berney and Danuser, Biophysical Journal, (2003) 84:3992-4010.

In one embodiment, the modified ligand binding molecule is labeled with a terbium chelate and an acceptor moiety (e.g., a green fluorophore). In some embodiments, the modified ligand binding molecule contains both an acceptor moiety and a terbium chelate (e.g., a LanthaScreen™ Terbium Chelate). In some embodiments a modified ligand binding molecule of the invention undergoes an about 10-fold change in RET ratio upon binding phosphate. In some embodiments a modified ligand binding molecule of the invention is sensitive at about 250 nM. In some embodiments a modified ligand binding molecule of the invention is robust at about 2.5 µM. In some embodiments of the invention, a modified ligand binding molecule provides at least 2, at least 3, at least 4, at least 5 or at least 10 times greater sensitivity than Malachite Green. Some embodiments of the invention provide assays and methods with a z' of greater than 0.5, greater than 0.6, greater than 0.7, greater than 0.8, or greater than 0.9. In some embodiments, the purity of the modified ligand binding molecule used in an assay or method of the invention is greater than 90%. In some embodiments of the invention, the modified ligand binding molecule is not substantially purified, e.g., from a cell lysate or clarified cell lysate.

Care may be taken to not disrupt the ligand binding region of a ligand binding molecule (e.g., a modified ligand binding molecule) in a way that the ligand bound versus the unbound ligand is not detectable or in a way that binding and/or releasing of a ligand by the ligand binding molecule (e.g., a modified ligand binding molecule) is abolished. In some embodiments, the ligand binding protein is modified to alter the binding specificity and/or binding affinity.

In particular embodiments, the ligand binding molecule is a fragment of a ligand binding protein, e.g., a fragment of a PBP. Many ligand proteins have been characterized (e.g., using crystallography studies) and the binding regions of the protein are known and characterized. Therefore, fragments of the ligand binding protein can be determined and produced which are capable of binding a ligand. In some embodiments of the invention, these ligand binding fragments of the ligand binding protein can be utilized as a modified ligand binding molecule as described herein.

In some embodiments, the ligand binding molecule does not bind phosphate. In some embodiments, the ligand binding molecule does not bind maltose.

Phosphate Binding Proteins

A number of proteins are known which specifically bind to phosphate (e.g., Pi). For example, transport of phosphate into and out of cells and organelles is executed by specific transport proteins. In bacterial cells, it is achieved by way of a high affinity transport system dependent on a phosphate-binding protein. Such proteins are able to specifically recognize inorganic phosphate, bind to it and transport it across cell membranes or between cellular compartments. Examples of such a proteins are the *E. coli* phosphate binding proteins, e.g., as encoded by the phoS gene of *E. coli*. This protein is located in the periplasm of *E. coli* as part of the Pi scavenging system of the bacterium, which operates under conditions of Pi starvation. Hence, binding affinity of this protein for Pi is high.

The phoS gene has been cloned and sequenced (Magota et al. J Bacteriol 1984, 157(3):909-17); Surin et al, J Bacteriol. 1984; 157(3): 772-778). Moreover, it has been determined that PBP binds Pi tightly (Medveczky and Rosenberg, Biochem Biophys Acta. 1969 192(2):369-71) and the crystal structure of the Pi-bound form has been solved to high resolution (Luecke and Quiocho, Nature. 1990 347(6291):402-6). These studies have shown *E. coli* PBP to consist of a monomeric protein of 35 kD separated into two domains, with a Pi-binding cleft between them. It is postulated that the Pi-binding cleft moves between open and closed positions upon Pi binding and release. Further examples of Pi transport proteins are reviewed by Torriani (Bioessays 1990, 12(8):371-6). A third class of Pi-binding proteins includes Pi-binding enzymes. Many enzymes bind Pi weakly and some are known to bind Pi strongly. Any phosphate binding protein can be utilized with the teachings of the present invention including, but not limited to, those described herein.

Hirschberg et al. (Biochemistry (1996) 37:10381-10385) present crystal structures for a A197C mutant of *Escherichia coli* PBP and the same mutant labeled with N-[2-(1-maleimidyl)ethyl]-7-(diethylamino)-coumarin-3-carboxamide (MDCC). Although not necessary, the crystal structure can be utilized for designing modified PBPs of the invention.

Another phosphate binding protein is a human plasma phosphate binding protein (HPBP). In some embodiments, the ligand-binding molecule of the invention is a human plasma phosphate binding protein (HPBP). See, e.g., Morales et al. *Structure, Vol* 14, 601-609, March 2006.

In some embodiments, the ligand binding molecule comprises a prokaryotic ligand binding protein or fragment thereof capable of binding the ligand, e.g., an *Escherichia coli* PBP such as encoded by a phoS gene. In some embodiments, the ligand binding molecule comprises a eukaryotic ligand binding protein or fragment thereof capable of binding the ligand, e.g., a HPBP such as those described in Morales et al. *Structure, Vol* 14, 601-609, March 2006. In some embodiments, the ligand binding molecule comprises a human ligand binding protein or fragment thereof capable of binding the ligand.

In the present application, it is shown that modification of a phosphate binding protein for attaching thereto a donor moiety (e.g., a Lanthanide chelate) and an acceptor moiety (e.g., a fluorescent or luminescent label) results in a modified phosphate binding protein which is sensitive to phosphate (e.g., Pi) and produces a shift in luminescence characteristics when Pi is bound. The modified protein may be used in a phosphate related assay which is capable of following the kinetics of biological reactions involving phosphate, as well as in conventional phosphate assays such as clinical assays and in pollution testing. One embodiment of the present invention provides a modified phosphate binding protein comprising a RET pair of moieties.

In some embodiments, the phosphate binding protein is modified in order to comprise at least one detectable label whose detectable characteristics alter upon a change in protein conformation which occurs on phosphate binding and/or phosphate release. In one embodiment, the change in the detectable characteristics is due to a conformational change upon binding or releasing phosphate (e.g., Pi) from a modified PBP, e.g., which changes the distance and/or orientation between a FRET pair. In one embodiment, the distance increases. In one embodiment, the distance decreases. In one embodiment, the orientation of the RET pair moieties changes. In one embodiment, the environment surrounding the donor and/or acceptor molecules changes.

A modified phosphate binding protein of the invention may be a modified form of any phosphate binding protein. In one embodiment, the PBP is involved in a protein from an active transport system which transfers Pi into and out of cells and cellular compartments. In one embodiment, the PBP is the *E. coli* phoS phosphate binding protein. PBPs can be modified as described herein, e.g., PBPs can be modified via native or non-native (e.g., inserted) cysteine amino acids.

In some embodiments of the invention, a modified PBP is derived from an *E. coli* phoS PBP. In some embodiments, a modified PBP is derived from SEQ ID NO: 1 or 2. In some embodiments, a modified PBP is SEQ ID NO: 1 or 2.

Some embodiments of the invention use an *E. coli* phoS PBP that comprises a native amino acid sequence. In one embodiment, the acceptor and/or donor moieties are attached to a PBP via thioether linkage. In one embodiment, the acceptor and/or donor moieties are attached to a PBP via mixed disulfide linkage. In one embodiment, the acceptor and/or donor moieties are attached to a PBP via an antibody.

In some embodiments, the acceptor and/or donor moiety of the RET pair is attached to the PBP via a thioester, thioether or mixed disulfide linkage. In some embodiments, amino acid 197 (numbering from the N-terminus of the mature PBP as shown in Magota et al (J Bacteriol. 1984, 157(3):909-17; e.g., SEQ ID NO:2) can be substituted with a cysteine. An attachment site for one member of a FRET pair can be at a cysteine residue substituted at position 197 in the amino acid sequence of a PBP, e.g., position 197 of SEQ ID NO:2. In some embodiments, the donor or acceptor moieties are attached to a cysteine substituted for an amino acid at a position selected from the group consisting of 47, 154, 185, 197, 201 and 268 (numbering from the N-terminus of the mature PBP as shown in Magota et al (J Bacteriol. 1984, 157(3):909-17; e.g., SEQ ID NO:2). In some embodiments, donor and/or acceptor moieties are attached to a cysteine substituted for or added adjacent to an amino acid, at a position selected from the group consisting of 42, 43, 44, 45, 46, 47, 48, 49, 50, 51, 149, 150, 151, 152, 153, 154, 155, 156, 157, 158, 159, 180, 181, 182, 183, 184, 185, 186, 187, 188, 189, 190, 191, 192, 193, 194, 195, 196, 197, 198, 199, 200 201, 264, 265, 266, 267, 268, 269, 270, 271, 272, and 273 (numbering from the N-terminus of the mature PBP as shown in Magota et al (J Bacteriol. 1984, 157(3):909-17; e.g., SEQ ID NO:2). For clarity, substitution includes the deletion of more than one amino acid. For example, a deletion of amino acids 195 to 198 would be considered a substitution of anyone of amino acids 195 to 198, e.g., 197. In some embodiments, an amino acid is substituted with a cysteine and the moiety is attached to the substituted cysteine, e.g., with a thiol-reactive label. In some embodiments, at least one cysteine is added adjacent to (e.g., inserted) one or more of the amino acids described herein. For example, a cysteine could be inserted adjacent to amino acid 47, 154, 185, 197, 201 or 268 (numbering from the N-terminus of the mature PBP as shown in Magota et al (J Bacteriol. 1984, 157(3):909-17; e.g., SEQ ID NO:2).

Various combinations for amino acid positions for attaching the donor and acceptor moieties (numbering from the N-terminus of the mature PBP as shown in Magota et al (J Bacteriol. 1984, 157(3):909-17; e.g., SEQ ID NO:2) are included as embodiments of the invention. The following are examples of "regions" where the acceptor or donor moieties can be attached (numbering from the N-terminus of the mature PBP as shown in Magota et al (J Bacteriol. 1984, 157(3):909-17; e.g., SEQ ID NO:2). Region 1 includes amino acids 42-51. Region 2 includes amino acids 149-159. Region 3 includes amino acids 180-191. Region 4 includes amino acids 192-201. Region 5 includes amino acids 264-273. These regions are presented as exemplary regions and in no way is the invention meant to be limited to these regions. In some embodiments of the invention, at least one acceptor moiety is located in one of regions 1 to 5 and at least one donor moiety is located in one of the other regions of 1 to 5. In some embodiments, at least one acceptor moiety is attached to region 1 and at least one donor moiety is attached to region 2, 3, 4 or 5. In some embodiments, at least one acceptor moiety is attached to region 2 and at least one donor moiety is attached to region 1, 3, 4 or 5. In some embodiments, at least one acceptor moiety is attached to region 3 and at least one donor moiety is attached to region 1, 2, 4 or 5. In some embodiments, at least one acceptor moiety is attached to region 4 and at least one donor moiety is attached to region 1, 2, 3, or 5. In some embodiments, at least one acceptor moiety is attached to region 5 and at least one donor moiety is attached to region 1, 2, 3, or 4.

In some embodiments, at least one donor moiety is attached to region 1 and at least one acceptor moiety is attached to region 2, 3, 4 or 5. In some embodiments, at least one donor moiety is attached to region 2 and at least one acceptor moiety is attached to region 1, 3, 4 or 5. In some embodiments, at least one donor moiety is attached to region 3 and at least one acceptor moiety is attached to region 1, 2, 4 or 5. In some embodiments, at least one donor moiety is attached to region 4 and at least one acceptor moiety is attached to region 1, 2, 3, or 5. In some embodiments, at least one donor moiety is attached to region 5 and at least one acceptor moiety is attached to region 1, 2, 3, or 4.

In some embodiments, the acceptor and donor moieties are attached to the same region, e.g. region 1, 2, 3, 4, or 5.

Moieties can be attached by any methods known in the art. This includes substituting cysteines, adding cysteines or using native cysteines to attach the moiety via thiol linkage. Moieties may also be attached via amines Additionally, moieties can be attached via noncovalent means/association including, but not limited to, antibodies, binding partners (such as biotin and streptavidin).

Care may be taken to not disrupt the phosphate binding region of the protein in a way that the phosphate bound versus the unbound PBP is not detectable or in a way that binding and/or releasing of phosphate by the PBP is abolished.

In one embodiment, RET increases upon phosphate (e.g., Pi) binding. In some embodiments, this change in RET will be greater than 10%, greater than 20%, greater than 30%, greater than 40%, greater than 50%, greater than 60%, greater than 70%, greater than 80%, greater than 90%, greater than 100%, greater than 200%, greater than 400%, greater than 750%, greater than 1000% or any other percentages as described herein. In some embodiments, this change in RET is greater than 10% and less than 1000%, greater than 100% and less than 400%, greater than 20% and less than 200%, greater than 200% and less than 750%, and greater than 400% and less than 1000%.

In one embodiment, RET decreases upon phosphate (e.g., Pi) binding. In some embodiments, this decrease will be greater than 10%, greater than 20%, greater than 30%, greater than 40%, greater than 50%, greater than 60%, greater than 70%, greater than 80%, greater than 90%, or any other percentage as described herein. In some embodiments, this change in RET is greater than 10% and less than 90%, greater than 20% and less than 60%, greater than 50% and less than 90%, or greater than 10% and less than 50%. In some embodiments, at least one member of the FRET pair is attached in the vicinity of the binding cleft of the E. coli PBP (e.g., within the binding cleft).

In one embodiment, the modified PBP is labeled with a terbium chelate and an acceptor moiety (e.g., a green fluorophore). In one embodiment, the modified PBP contains both an acceptor moiety and a terbium chelate (e.g., a LanthaScreen™ Terbium Chelate). In some embodiments a modified PBP of the invention undergoes an about 10-fold change in RET ratio upon binding phosphate. In some embodiments a modified PBP of the invention is sensitive at about 250 nM. In some embodiments a modified PBP of the invention is robust at about 2.5 μM. In some embodiments of the invention, a modified PBP provides at least 2, at least 3, at least 4, at least 5 or at least 10 times greater sensitivity than Malachite Green. In some embodiments, a modified PBP provides 2 to 10 times greater, 3 to 5 times greater, 4 to 10 times greater sensitivity than Malachite Green. Some embodiments of the invention provide assays and methods with a z' of greater than 0.5, greater than 0.6, greater than 0.7, greater than 0.8, or greater than 0.9. Some embodiments of the invention provide assays and methods with a z' of between 0.5 and 0.9, 0.5 to 0.7, 0.6 to 0.9, or 0.7 to 0.99.

In some embodiments, the purity of the modified PBP used in an assay or method of the invention is greater than 90%. In some embodiments of the invention, the modified PBP is not substantially purified, e.g., from a cell lysate or clarified cell lysate.

Binding Partner

As used herein, binding partners refer to binding molecules that bind the ligand binding molecule, but is not meant to include the ligand to be detected. A "binding partner" is a compound (e.g., an antibody) that has affinity for another compound (e.g., a ligand binding molecule) such that the binding partner and the compound are capable of forming a complex when bound. For example, a first binding partner can be a monoclonal antibody that recognizes an epitope on the ligand binding domain. In some embodiments, the epitope is a native epitope found on the ligand binding molecule. In some embodiments, the epitope is introduced or engineered to the ligand binding molecule. Epitopes that may be used include, but are not limited to, a histidine tag (e.g., 6×histidine) (SEQ ID NO: 5); c-myc (e.g., an amino acid segment of the human protooncogene myc (e.g., EQKLISEEDL (SEQ ID NO: 3)); haemoglutinin tag (e.g., from an influenza hemagglutinin protein (e.g., YPYDVPDYA (SEQ ID NO: 4)); digoxigenin (a small organic molecule that can be covalently added to proteins or nucleic acids); and biotin.

Some embodiments of the invention utilize antibodies labeled with a lanthanide metal complex (e.g., comprising a Tb chelate) following standard protocols (e.g., supplied with a commercial chelate reagent). In some embodiments, antibodies are labeled "in situ" through association with species-specific antibodies (e.g., Tb-labeled anti-IgG) that bind to an anti-ligand-binding-molecule antibody. In some embodiments, assays of the invention may be read using standard "LanthaScreen™" settings, e.g., as described in the "LanthaScreen™ User's Guide" (Invitrogen, California).

Accordingly, in one aspect, the invention provides compositions that include a binding partner. A binding partner can be labeled with a luminescent metal complex (e.g., Tb or Europium). In some embodiments, the binding partner can be labeled with an acceptor moiety (e.g., fluorescent). The present invention also provides mixtures of binding partners. For example, a composition can include a first binding partner and a second binding partner. A first binding partner can comprise a luminescent metal complex while the second binding partner can comprise an acceptor moiety (e.g., fluorescent). In some embodiments, the first binding partner can comprise a fluorescent acceptor moiety, while the second binding partner can comprise a luminescent metal complex wherein both binding partners will bind the ligand binding molecule.

Typically, the affinity (e.g., apparent Kd) of a first binding partner for a ligand binding molecule is about 1 mM or less, e.g., about 10 μM or less, or about 1 μM or less, or about 0.1 μM or less, or 10 nM or less, or 1 nM or less, or 0.1 nM or less. In some embodiments, the affinity of a first binding partner for a ligand binding molecule is between about 1 mM to 0.1 nM, between about 10 μM to 1 μM, and between about 1 μM to 1 nM, As one of skill in the art will recognize, one can systematically adjust experimental parameters, e.g., concentrations of assay components, reaction times, temperatures, and buffers, depending on the Kd of the binding partner for the ligand binding molecule, to obtain a desired combination of conditions and cost-effectiveness.

A binding partner can be a protein, polypeptide, a polynucleotide, a lipid, a phospholipid, a polysaccharide, or an organic molecule. Examples of specific protein or polypeptide binding partners include an antibody, a protein, or an enzymatically or chemically-synthesized or modified polypeptide sequence (e.g., a polypeptide sequence derived from a protein, modified from a protein, or designed and synthesized de novo.) A protein or polypeptide binding partner may be linear or cyclic. An organic molecule binding partner can be a small organic molecule.

In some embodiments, a binding partner comprises either a luminescent metal complex or an acceptor moiety (e.g., fluorescent). In some embodiments, one binding partner can comprise a luminescent metal complex and another can comprise an acceptor moiety (e.g., fluorescent), e.g., a first binding partner comprises a luminescent metal complex and a second binding partner comprises an acceptor moiety (e.g., fluorescent).

In one embodiment, an antibody can be labeled with a luminescent metal chelate and a ligand binding molecule that the antibody binds can be labeled with an acceptor moiety (e.g., fluorescent).

Binding partners can be prepared and purified by a number of methods known to those of ordinary skill in the art. For example, antibodies, including monoclonal antibodies and antibody fragments, can be prepared by a number of methods known to those of skill in the art, or can be purchased from a variety of commercial vendors, including Serotec (Raleigh, N.C.), Abcam (Cambridge, Mass.), R&D Systems, Cambridge Antibody Technologies, and Covance Research Products (Denver, Colo.).

In general, an antigen for which an antibody is desired is prepared, e.g., recombinantly, by chemical synthesis, or by purification of a native protein, and then used to immunize animals. For example, polypeptides or proteins containing a particular amino acid sequence and/or post-translational modification (e.g., phosphorylation) can be prepared by solid-phase chemical synthesis in order to raise an antibody specific for the sequence and/or post-translational modification. Various host animals including, for example, rabbits, chickens, mice, guinea pigs, goats, and rats, can be immunized by injection of the antigen of interest. Depending on the host species, adjuvants can be used to increase the immunological response and include Freund's adjuvant (complete and/or incomplete), mineral gels such as aluminum hydroxide, surface-active substances such as lysolecithin, pluronic polyols, polyanions, peptides, oil emulsions, keyhole limpet hemocyanin, and dinitrophenol. Polyclonal antibodies are contained in the sera of the immunized animals. Monoclonal antibodies can be prepared using standard hybridoma technology. In particular, monoclonal antibodies can be obtained by any technique that provides for the production of antibody molecules by continuous cell lines in culture as described, for example, by Kohler et al. (1975) Nature 256:495-497, the human B-cell hybridoma technique of Kosbor et al. (1983) Immunology Today 4:72, and Cote et al. (1983) Proc. Natl. Acad. Sci. USA 80:2026-2030, and the EBV-hybridoma technique of Cole et al., Monoclonal Antibodies and Cancer Therapy, Alan R. Liss, Inc. pp. 77-96 (1983). Such antibodies can be of any immunoglobulin class including IgM, IgG, IgE, IgA, IgD, and any subclass thereof. A hybridoma producing the monoclonal antibodies of the invention can be cultivated in vitro or in vivo. Chimeric antibodies can be produced through standard techniques.

Antibody fragments that have specific binding affinity for an antigen can be generated by known techniques. Such antibody fragments include, but are not limited to, F(ab')2 fragments that can be produced by pepsin digestion of an antibody molecule, and Fab fragments that can be generated by reducing the disulfide bridges of F(ab')2 fragments. Alternatively, Fab expression libraries can be constructed. See, for example, Huse et al. (1989) Science 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

Once produced, antibodies or fragments thereof can be tested for recognition of (and affinity for) a ligand binding molecule (e.g., a PBP) by standard immunoassay methods including, for example, enzyme-linked immunosorbent assay (ELISA) or radioimmuno assay (RIA). See, Short Protocols in Molecular Biology, eds. Ausubel et al., Green Publishing Associates and John Wiley & Sons (1992). Suitable antibodies typically will have a Kd for an antigen (e.g., a ligand binding molecule) of about 1 mM or less, e.g., about 10 µM or less, or about 1 µM or less, or about 0.1 µM or less, or about 10 nM or less, or about 1 nM or less, or about 0.1 nM or less. In some embodiments, an antibody will have a Kd for an antigen between about 1 mM to 0.1 nM, between about 10 µM to 1 µM, and between about 1 µM to 1 nM.

Other polypeptides in addition to antibodies are useful as first or second binding partners and can also be prepared and analyzed using standard methods. By way of example and not limitation, polypeptides, proteins and antibodies can be obtained by extraction from a natural source (e.g., from isolated cells, tissues or bodily fluids), by expression of a recombinant nucleic acid encoding the protein or polypeptide, or by chemical synthesis. Polypeptides or proteins can be produced by, for example, standard recombinant technology, using expression vectors encoding the proteins or polypeptides. The resulting polypeptides then can be purified. Expression systems that can be used for small or large scale production of polypeptides include, without limitation, microorganisms such as bacteria (e.g., E. coli and B. subtilis) transformed with recombinant bacteriophage DNA, plasmid DNA, or cosmid DNA expression vectors; yeast (e.g., S. cerevisiae) transformed with recombinant yeast expression vectors; insect cell systems infected with recombinant virus expression vectors (e.g., baculovirus); plant cell systems infected with recombinant virus expression vectors (e.g., tobacco mosaic virus) or transformed with recombinant plasmid expression vectors (e.g., Ti plasmid); or mammalian cell systems (e.g., primary cells or immortalized cell lines such as COS cells, Chinese hamster ovary cells, HeLa cells, human embryonic kidney 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter).

Suitable methods for purifying the polypeptides or proteins, including antibodies or binding fragments thereof, of the invention can include, for example, affinity chromatography, immunoprecipitation, size exclusion chromatography, and ion exchange chromatography. See, for example, Flohe et al. (1970) Biochim Biophys. Acta. 220:469-476, or Tilgmann et al. (1990) FEBS 264:95-99. The extent of purification can be measured by any appropriate method, including but not limited to: column chromatography, polyacrylamide gel electrophoresis, or high-performance liquid chromatography.

Polypeptides and proteins as binding partners can also be prepared using solid phase synthesis methods, see, e.g., PCT Publication No. WO 03/01115 and U.S. Pat. No. 6,410,255. For ease of synthesis and cost considerations, polypeptides synthesized chemically can be typically between 3 to 50 amino acids (e.g., 3 to 30, 3 to 20, 3 to 15, 5 to 30, 5 to 20, 5 to 15, 8 to 20, 8 to 15, 10 to 10, 10 to 15 or 10 to 12 amino acids in length). In the polypeptides and proteins of the invention, a great variety of amino acids can be used. Suitable amino acids include natural, non-natural, and modified (e.g., phosphorylated) amino acids. Amino acids with many different protecting groups appropriate for immediate use in the solid phase synthesis of peptides are commercially available.

Polynucleotides useful as binding partners can be produced by standard techniques, including, without limitation, common molecular cloning and chemical nucleic acid synthesis techniques. For example, polymerase chain reaction (PCR) techniques can be used. PCR refers to a procedure or technique in which target nucleic acids are enzymatically amplified. Sequence information from the ends of the region of interest or beyond typically is employed to design polynucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in PCR Primer: A Laboratory Manual, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis Genetic Engineering News, 12(9):1 (1992); Guatelli et al., Proc. Natl. Acad. Sci. USA, 87:1874-1878 (1990); and Weiss, Science, 254:1292 (1991).

Polynucleotides of the invention also can be chemically synthesized, either as a single nucleic acid molecule (e.g., using automated DNA synthesis in the 3' to 5' direction using phosphoramidite technology) or as a series of smaller polynucleotides. For example, one or more pairs of long polynucleotides (e.g., >100 nucleotides) can be synthesized that contain the desired sequence, with each pair containing a short segment of complementarity (e.g., about 15 nucleotides) such that a duplex is formed when the polynucleotide pair is annealed. DNA polymerase is used to extend the polynucleotides, resulting in a single, double-stranded polynucleotide.

Polynucleotides of the invention also can be obtained by mutagenesis. For example, polynucleotides can be mutated using standard techniques including polynucleotide-directed mutagenesis and site-directed mutagenesis through PCR. See Short Protocols in Molecular Biology, Chapter 8, Green Publishing Associates and John Wiley & Sons, edited by Ausubel et al., 1992.

In some embodiments of the invention, the binding partner(s) is utilized to bring a detectable moiety (e.g., a member of a RET pair) in close proximity to the ligand binding molecule. In some embodiments, the ligand binding molecule is directly labeled with one member of a RET pair and a binding partner provides the other member of the RET pair, e.g., see FIG. 12B. In one embodiment, two binding partners provide both members of a RET pair to the ligand binding molecule. In some embodiments of the invention, detectable energy transfer or lack thereof between the RET is modulated or changed by the release and/or binding of the ligand by the ligand binding molecule.

Assays, methods, and modified ligand binding molecules of the invention may utilize none, one, two or more binding partners.

Luminescent Metal Complex

A luminescent metal complex can act as a donor fluorophore in a RET or TR-RET assay. A luminescent metal complex is useful in the present methods because its excited state lifetime is typically on the order of milliseconds or hundreds of microseconds rather than nanoseconds; a long excited state lifetime allows detection to be monitored after the decay of background fluorescence and/or interference from light-scattering.

Methods for covalently linking a luminescent metal complex to a variety of molecules and proteins are known to those of skill in the art, e.g., PCT Publication Nos. WO 96/23526; WO 01/09188, WO 01/08712, and WO 03/011115; U.S. Patent Publication No. 20050064485 and U.S. Pat. Nos. 5,639,615; 5,656,433; 5,622,821; 5,571,897; 5,534,622; 5,220,012; 5,162,508; and 4,927,923.

A luminescent metal complex includes a metal liganding moiety, one or more lanthanide metal ions, and optionally linkers, spacers, and organic antenna moieties.

Metal Liganding Moiety

A metal liganding moiety coordinates one or more lanthanide metal ions to form a metal complex. Typically, a metal liganding moiety includes one or more metal coordinating moieties X, where X is a heteroatom electron-donating group capable of coordinating a metal cation, such as $O^-$, $OH$, $NH_2$, $OPO_3^{2-}$, $NHR$, or $OR$ where R is an aliphatic group.

A metal liganding moiety can be a chelating moiety or a cryptand moiety. If a lanthanide metal ion is coordinated to a chelating moiety, the complex is referred to as a "metal chelate." If a lanthanide metal ion is coordinated to a cryptand moiety, the complex is referred to as a "metal cryptand."

A metal chelate should be stable to exchange of the lanthanide ion. Metal chelates in most cases, but not all, will have a formation constant ($K_f$) of greater than $10^{10}$ $M^{-1}$. A variety of useful chelating moieties are known to those of skill in the art. Typical examples of chelating moieties include: EDTA, DTPA, TTHA, DOTA, NTA, HDTA, DTPP, EDTP, HDTP, NTP, DOTP, DO3A, DOTAGA, and NOTA.

In some embodiments, a luminescent metal chelate can have the following structures:

or

wherein A represents an organic antenna moiety;
L represents a linker;
S represents a spacer;
n can be 0 or 1;
C represents a metal chelating moiety; and
M represents a lanthanide metal ion coordinated to C.

Figure 3:
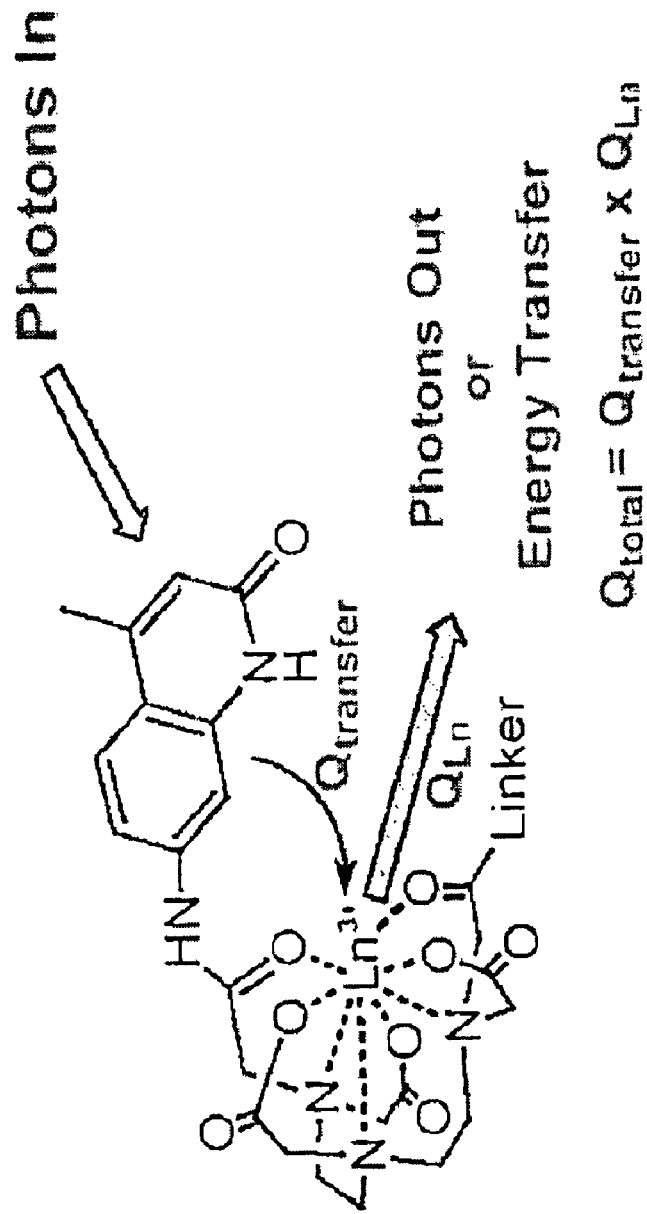
FIG. 3 represents a structure of a lanthanide metal chelate comprising an organic antenna moiety and shows the transfer of energy from the organic antenna moiety to the lanthanide metal ion.

For illustrative examples of luminescent metal chelates, see FIG. 3.

Cryptates are formed by the inclusion of a lanthanide cation into a tridimensional organic cavity, leading to highly stable complexes. A variety of useful cryptand moieties are known to those of skill in the art. Examples of cryptand moieties useful in the present methods include: trisbypyridine (TBP, e.g., TBP pentacarboxylate), and pyridine bipyridine (e.g., pyridine bipyridine tetracarboxylate).

Chelating and cryptand moieties can be synthesized by a variety of methods known to those of skill in the art or may be purchased commercially, e.g., U.S. Pat. Nos. 5,639,615; 5,656,433; 5,622,821; 5,571,897; 5,534,622; 5,220,012; 5,162,508; and 4,927,923; and PCT Publication Nos. WO 96/23526 and WO 03/011115.

Lanthanide Metal Ions

Metal liganding moieties coordinate one or more lanthanide metal ions to form a metal complex. Lanthanide metal ions are useful because their special electronic configuration shields the optically active electrons, resulting in characteristic line type emissions. As the electronic transitions of the metal ions are forbidden by quantum mechanics rules, the emission lifetimes of these ions are typically long (from us to msec).

Useful lanthanide metal ions include Sm(III), Ru(III), Eu (III), Gd(III), Tb(III), and Dy(III). Methods for complexing a metal ion to a chelating or cryptand moiety are known to those of skill in the art, e.g., PCT Publication Nos. WO 96/23526 and WO 03/011115.

Antenna Moieties

A luminescent metal complex can optionally include an antenna moiety (e.g., an organic antenna moiety). An organic antenna moiety typically has a conjugated electronic structure so that it can absorb light. The absorbed light is transferred by intramolecular non-radiative processes from the singlet to the triplet excited state of the antenna moiety, then from the triplet state to the emissive level of the lanthanide ion, which then emits characteristically long-lived luminescence (FIG. 3). It should be noted that some metal liganding moieties can absorb light without the inclusion of an organic antenna moiety. For example, certain cryptand moieties that contain conjugated organic moieties, such as tribipyridine pentacarboxylate, do not require the inclusion of a discrete organic antenna moiety.

In some embodiments, an organic antenna moiety can be a polynuclear heterocyclic aromatic compound. The polynuclear heterocyclic aromatic compound can have two or more fused ring structures. Examples of useful organic antenna moieties include rhodamine 560, fluorescein 575, fluorescein 590, 2-quinolone, 4-quinolone, 4-trifluoromethylcoumarin (TFC), 7-diethyl-amino-coumarin-3-carbohydrazide, 7-amino-4-methyl-2-coumarin (carbostyril 124, CS 124), 7-amino-4-methyl-2-coumarin (coumarin 120), 7-amino-4-trifluoromethyl-2-coumarin (coumarin 124), CS124-DTPA-Phe-NCS-Tb (U.S Patent Publication No. US20050064485), CS124-DTPA-EMCH-Tb (U.S Patent Publication No. US20050064485) and aminomethyltrimethylpsoralen.

Compounds useful as organic antenna moieties can be synthesized by methods known to those of skill in the art or purchased commercially, e.g., U.S. Pat. Nos. 5,639,615; 5,656,433; 5,622,821; 5,571,897; 5,534,622; 5,220,012; 5,162,508; and 4,927,923.

Linkers, Spacers

Linkers and spacers can optionally be included in a luminescent metal complex. A Linker (L) functions to link a luminescent metal complex to a molecule. For example the linker can attach a luminescent metal complex to a protein, e.g., to an amino acid of the protein via a reaction with an amine or thiol, e.g., producing an amide, thioether, or disulfide linkage. In some embodiments, a L can link an acetate, amine, amide, carboxylate, or methylene functionality on a metal liganding moiety to a molecule (e.g., a PBP). One of skill in the art can design Ls to react with a number of functionalities on molecules (e.g., proteins or PBPs), including, without limitation, amines, acetates, thiols, alcohols, ethers, esters, ketones, and carboxylates. In some embodiments where the molecule is a polypeptide, a L can cap the N-terminus, the C-terminus, or both N- and C-termini, as an amide moiety. Other exemplary L capping moieties include sulfonamides, ureas, thioureas and carbamates. Ls can also include linear, branched, or cyclic alkanes, alkenes, or alkynes, and phosphodiester moieties. The L may be substituted with one or more functional groups, including ketone, ester, amide, ether, carbonate, sulfonamide, or carbamate functionalities. Specific Ls contemplated also include NH—CO—NH—; —CO—(CH$_2$)$_n$—NH—, where n=1 to 10; —NH—Ph-; —NH—(CH$_2$)$_n$—, where n=1 to 10; —CO—NH—; —(CH$_2$)$_n$—NH—, where n=1 to 10; —CO—(CH$_2$)$_n$—NH—, where n=1 to 10; and —CS—NH—. Additional examples of Ls and synthetic methodologies for incorporating them into metal complexes, particularly metal complexes linked to polypeptides, are set forth in WO 01/09188, WO 01/08712, and WO 03/011115. In some embodiments, a disulfide linkage is utilized.

A Spacer (S) can connect an organic antenna moiety to a metal liganding moiety. In some embodiments, an S can link an acetate, amine, or methylene functionality on a metal liganding moiety to an organic antenna moiety. One of skill in the art can design Ss to react with a number of functionalities on organic antenna moieties and on metal liganding moieties, including, without limitation, amines, acetates, thiols, alcohols, ethers, esters, ketones, and carboxylates. Ss can include linear, branched, or cyclic alkanes, alkenes, or alkynes, and phosphodiester moieties. The S may be substituted with one or more functional groups, including ketone, ester, amide, ether, carbonate, sulfonamide, or carbamate functionalities. Specific Ss contemplated also include NH—CO—NH—; —CO—(CH$_2$)$_n$—NH—, where n=1 to 10; —NH-Ph-; —NH—(CH$_2$)$_n$—, where n=1 to 10; —CO—NH—; —(CH$_2$)$_n$—NH—, where n=1 to 10; —CO—(CH$_2$)$_n$—NH—, where n=1 to 10; and —CS—NH—.

Donor and Acceptor Moieties

A modified ligand binding molecule (e.g., a modified PBP) of the invention can include an acceptor moiety (e.g., fluorescent). An acceptor moiety can act as an acceptor in RET or TR-RET based assays. In general, an acceptor moiety (e.g., fluorescent) should, but does not necessarily exhibit a good quantum yield and a large extinction coefficient; should, but is not necessarily resistant to collisional quenching and bleaching; and should, but is not necessarily easily conjugated to a variety of ligand binding molecules (e.g., PBPs) by methods known to those having ordinary skill in the art. Suitable fluorophores include, without limitation, fluorescein, rhodamine, FITCs (e.g., fluorescein-5-isothiocyanate), 5-carboxyfluorescein, 6-carboxyfluorescein, 5,6-carboxyfluorescein, 7-hydroxycoumarin-3-carboxamide, 6-chloro-7-hydroxycoumarin-3-carboxamide, dichlorotriazinylaminofluorescein, tetramethylrhodamine-5-isothiocyanate, tetramethylrhodamine-6-isothiocyanate, succinimidyl ester of 5-carboxyfluorescein, succinimidyl ester of 6-carboxyfluorescein, 5-carboxytetramethylrhodamine, 6-carboxymethylrhodamine, and 7-amino-4-methylcoumarin-3-acetic acid. Other suitable fluorophores include the CY fluorophore family CY3 dye, CY3B dye, CY3.5 dye, CY5 dye; available from GE Healthcare, Chalfont St. Giles, United Kingdom); the ALEXA FLUOR dye family (available from Invitrogen, Carlsbad, CA); the BODIPY dye family (available from Invitrogen, Carlsbad, CA); carbopyronins; squarines; cyanine/indocyanines; benzopyrylium heterocycles; and amide-bridged benzopyryliums.

Fluorescent proteins and mutants can also be used as fluorescent acceptor moieties. Examples include firefly, bacterial, or click beetle luciferases, aequorins, and other photoproteins (for example as described in U.S. Pat. Nos. 5,221,623; 5,683, 888; 5,674,713; 5,650,289; and 5,843,746. GFP and GFP mutants are particularly useful in applications using Tb(III)-containing metal complexes. A variety of mutants of GFP from *Aequorea victoria* have been created that have distinct spectral properties, including improved brightness, and enhanced expression and folding in mammalian cells compared to the native GFP (e.g., see Table 7 of U.S. Pat. No.

6,410,255; Green Fluorescent Proteins, Chapter 2, pages 19 to 47, edited by Sullivan and Kay, Academic Press; and U.S. Pat. Nos. 5,625,048; 5,777,079; and 5,804,387. Fluorescent proteins can be attached chemically or a ligand binding protein coding region can be engineered to express a fusion protein comprised of a fluorescent protein. Fluorescent proteins can be used as the acceptor moiety, donor moiety or both.

In some embodiments, an acceptor moiety (e.g., fluorescent) for use in multiplex assays exhibits characteristics useful for RET/TR-RET applications. For TR-RET applications, a region of the acceptor moiety's (e.g., a fluorophore's) absorbance spectra should overlap with a region of a donor moiety's (e.g., a luminescent metal chelate's) emission spectra, while a region of the acceptor's emission spectra should not overlap substantially with a region of the donor's emission spectra. For example, regions of the emission spectra of an organic-antenna-Tb(III)-chelate-containing metal complex do not significantly overlap with the emission spectra for fluorescein or rhodamine.

Examples of suitable acceptor fluorophores in TR-RET assays using Tb(III)-containing luminescent metal complexes include: fluorescein (and its derivatives); rhodamine (and its derivatives); ALEXA FLUOR dyes 488, 500, 514, 532, 546, 555, 568 (available from Molecular Probes); BODIPY dyes FL, R6G, and TMR (available from Molecular Probes); CY3 dye and CY3B dye (available from Amersham Biosciences), and IC3 (available from Dojindo Molecular Technologies, Gaithersburg, MD). Examples of suitable acceptor fluorophores in TR-RET assays using Eu(III)-containing luminescent metal complexes include: ALEXA FLUOR dyes 594, 610, 633, 647, and 660 (available from Molecular Probes); BODIPY dyes TR, 630/650, and 650/665 (available from Molecular Probes); CY5dye (available from Amersham Biosciences) and IC5 (available from Dojindo Molecular Technologies). Any fluorescent protein from any species could also serve as a suitable acceptor e.g., wild type (native or recombinant) or a mutant of Green Fluorescein Protein e.g., from Aequorea Victoria, a blue fluorescent protein (BFP), a red fluorescent protein (RFP), a cyan fluorescent protein (CFP), or a yellow fluorescent protein (YFP). Suitable fluorophores for use in the present invention are commercially available, e.g., from Invitrogen, Carlsbad, Calif., Attotec (Germany), Amersham, and Biosearch Technologies (Novato, Calif.). Methods for incorporating fluorophores into proteins are known to those of skill in the art; e.g., U.S. Pat. Nos. 5,898,069 and 6,410,255.

In some embodiments, the acceptor moiety is not a GFP. In some embodiments, the acceptor moiety is not an aequorin protein. In some embodiments, the acceptor moiety is not a protein.

In some embodiments, the donor moiety is not a GFP. In some embodiments, the donor moiety is not an aequorin protein. In some embodiments, the donor moiety is not a protein.

RET and TR-RET

Some embodiments of the present invention take advantage of resonance energy transfer between a donor moiety (e.g., a luminescent metal chelate) and an acceptor moiety (e.g., fluorescent moiety). In some embodiments, a donor luminescent metal chelate is excited by light of appropriate wavelength and intensity (e.g., within the donor antenna moiety's excitation spectrum) and under conditions in which direct excitation of the acceptor fluorophore is minimized The donor moiety (e.g., a luminescent chelate) then transfers the absorbed energy (e.g., by non-radiative means) to the acceptor moiety (e.g., fluorescent), which subsequently re-emits some of the absorbed energy, e.g., as fluorescence emission at one or more characteristic wavelengths. In TR-RET applications, the re-emitted radiation is not measured until after a suitable delay time, e.g., 25, 50, 75, 100, 150, 200, 300, 25 to 300, 25 to 150, 100 to 300, or 100 to 200 microseconds to allow decay of background fluorescence, light scattering, or other luminescence, such as that caused by the plastics used in microtiter plates.

In some embodiments, RET can be manifested as a reduction in the intensity of the luminescent signal from the donor moiety (e.g., a luminescent metal complex) and/or an increase in emission of fluorescence from the acceptor (e.g., fluorescent) moiety. In some embodiments, the efficiency of RET is dependent on the separation distance and/or the orientation of a luminescent metal complex and acceptor fluorescent moiety, the luminescent quantum yield of the donor metal ion, the spectral overlap with the acceptor fluorescent moiety, and the extinction coefficient of the acceptor fluorophore at the wavelengths that overlap with the donor's emission spectra. Forster derived the relationship:

$$E = (F^\circ - F)/F^\circ = Ro^6/(R^6 + Ro^6)$$

where E is the efficiency of RET, F and F° are the fluorescence intensities of the donor in the presence and absence of the acceptor, respectively, and R is the distance between the donor and the acceptor. Ro, the distance at which the energy transfer efficiency is 50% of maximum is given (in Å) by:

$$Ro = 9.79 \times 10^3 (K^2 Q J n^{-4})^{1/6}$$

where $K^2$ is an orientation factor having an average value close to 0.67 for freely mobile donors and acceptors, Q is the quantum yield of the unquenched fluorescent donor, n is the refractive index of the intervening medium, and J is the overlap integral, which expresses in quantitative terms the degree of spectral overlap. The characteristic distance Ro at which RET is 50% efficient depends on the quantum yield of the donor, the extinction coefficient of the acceptor, the overlap between the donor's emission spectrum and the acceptor's excitation spectrum, and the orientation factor between the two fluorophores.

Changes in the degree of RET can be determined as a function of a change in a ratio of the amount of luminescence/fluorescence from the donor and acceptor moieties, a process referred to as "ratioing." By calculating a ratio, the assay is less sensitive to, for example, well-to-well fluctuations in substrate concentration, photobleaching and excitation intensity, thus making the assay more robust. This is of particular importance in automated screening applications where the quality of the data produced is important for its subsequent analysis and interpretation, see, e.g., U.S. Pat. Nos. 6,410, 255; 4,822,733; 5,527,684; and 6,352,672.

For example, in some embodiments of the method, a ratiometric analysis is performed, wherein a ratio of luminescence/fluorescent emission at two different wavelengths is compared between a test sample and a control sample. In a typical TR-RET-based assay, the two wavelengths can correspond to an emission maximum for a luminescent metal complex and a fluorescent acceptor moiety. In some embodiments, an emissions ratio of the control sample will be about 1.5, 2, 3, 4, 5, 7, 10, 15, 20, 25, 30, 40, 50, 100, 1.5 to 100, 1.5 to 25, 10 to 40, 20 to 100, 1.5 to 100, or 50 to 100 times larger or smaller than the emissions ratio of a test sample.

Ligand Detecting Assays

Figure 1:
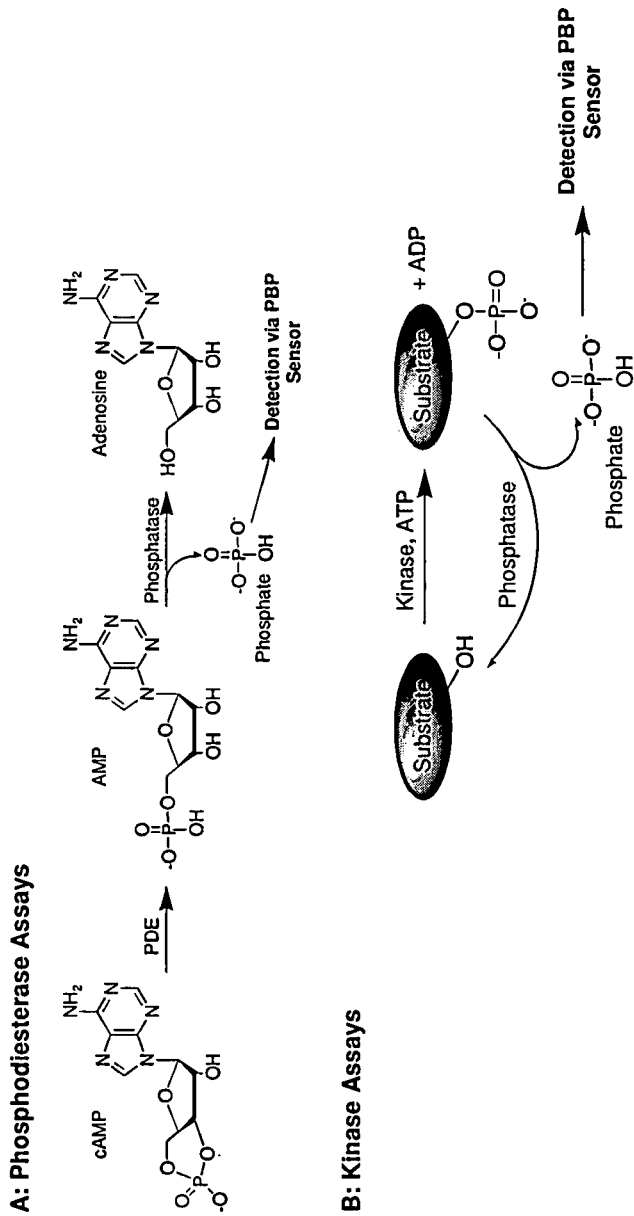
FIG. 1A shows an example of a phosphodiesterase assay and how it can be coupled to a phosphate detection assay.
FIG. 1B shows an example of a kinase assay and how it can be coupled to a phosphate detection assay.

Some ligand binding molecules (e.g., PBPs) of the invention can be used to measure the activity of any enzyme or reaction that produces or consumes a ligand (e.g., phosphate), such as phosphatases, phosphodiesterases (e.g., coupled reaction), phosphorylases, ATPase, GTPases, and prenyl transferases (e.g., coupled reaction). Therefore, some embodiments of the invention provide assays involving phosphatases, phosphodiesterases (e.g., coupled reactions/assays), phosphorylases, ATPase, GTPases, prenyl transferases (e.g., coupled reactions/assays). In some embodiments, modified PBPs of the invention are used to measure phosphate that is a direct product of or directly consumed by a reaction of interest, e.g., a phosphatase reaction. In some embodiments, modified PBPs of the invention are used to measure phosphate that is an indirect product of or indirectly consumed by a reaction of interest, e.g., a kinase reaction coupled to a phosphatase reaction (FIG. 1).

The present application describes various examples of methods, assays and assay formats. One skilled in the art will readily recognize other formats and assays and various permutations based on the teaching herein. The present invention encompasses and contemplates these embodiments. For example, PBP is used herein as an example of a ligand binding molecule and the assays and assay formats described herein using a PBP can be utilized for other ligand binding molecules.

In one aspect of the invention, there is provided a method for detecting phosphate in a sample comprising the steps of: (a) contacting a sample with a modified ligand binding protein (e.g., a PBP) comprising a donor and acceptor moiety of a FRET pair; (b) exposing (a) to a wavelength of light that excites the donor moiety; and (c) detecting energy (e.g., light) emitted from the acceptor moiety. In one embodiment, the method further comprises detecting both the energy (e.g., light/fluorescence) emitted from the donor and acceptor moieties. In some embodiments, a ratiometric calculation can be calculated between the light emitted from the donor versus the acceptor moiety.

In some embodiments, a phosphatase assay can release a phosphate which can then be detected and measured using a modified PBP or other ligand binding molecule of the present invention, thereby directly measuring and/or detecting the phosphatase activity. Embodiments of the invention can be used in reactions that directly liberate or consume phosphate or in reactions that can be coupled through another reaction to generate or consume phosphate.

In some embodiments, the assay is a coupled assay. For example, a kinase assay can result in the phosphorylation of a protein. Then a phosphatase can be utilized which removes the phosphate from the phosphorylated protein and then a modified PBP of the present invention can be utilized to detect and/or measure the removed phosphate, thereby indirectly measuring and/or detecting the kinase activity, e.g., see, FIG. 1B.

Other embodiments of the invention provide a coupled phosphodiesterase assay. For example, cAMP is converted to AMP by phosphodiesterase. Then AMP is converted to adenosine and phosphate via an appropriate phosphatase. The phosphate is then detected using a modified PBP of the invention, e.g., see, FIG. 1A for a graphic representation of a coupled phosphodiesterase assay. For example, the above described coupled phosphodiesterase assay can be used to measure amounts or activity of a phosphodiesterase enzyme or measure the amounts of cAMP in a sample.

Therefore, the methods and assays of the invention can be utilized to measure or detect a variety of compounds, reactions or events.

The invention provides, in part, methods for monitoring the progression of a reaction. Ligand binding proteins of the present invention can exhibit detectable changes upon binding and/or release of the ligand. These changes can be utilized to monitor a reaction. The reaction can involve the production or reduction of the ligand in a sample or reaction. The concentration of the ligand can be measured in real-time (e.g. kinetic measurements), as time points or as end points, usually after a period of time. Ligand binding molecules of the invention can be added directly to a reaction where monitoring, detecting or quantitating a particular ligand is desired. For example, a ligand binding molecule (e.g., a PBP) of the invention can be added directly to a phosphatase reaction (e.g. at the start of the reaction). In some embodiments, the concentration of the ligand (e.g., phosphate) can be measured directly in the reaction. In some embodiments, an aliquot of the reaction is removed at a desired time point and the ligand concentration and/or quantity is measured. In some embodiments, the ligand binding molecule of the invention is contacted with the reaction after the reaction has been started or even stopped and the ligand concentration and/or quantity is measured. In some embodiments, more than one ligand binding molecule of the invention is utilized to monitor the concentration of one or multiple ligands.

Ligand binding molecules of the invention allow measuring and/or monitoring of a reaction and/or the concentration of the ligand. Ligand binding molecules of the invention allow for versatile types of measurements, e.g., real-time (e.g. kinetic measurements), as time points or as end points. Typically real-time or kinetic measurements are carried out by contacting the ligand binding molecule of the invention with a reaction to be monitored. For example, the ligand binding molecule is added to the reaction mixture, e.g. at the start of the reaction. Then measurements are conducted at desired time points directly in the reaction. Another method is to remove aliquots from the reaction (e.g., at desired time points) and measure the ligand concentration using a ligand binding molecule of the invention. Using certain embodiments of the present invention, it is possible to follow the kinetics of biological systems due to the rapid reaction time of the method.

In some embodiments related to coupled assays involving phosphatase, it is desired that the phosphatase exhibits minimal activity towards a substrate molecule, and high activity towards a product molecule. For example, in a kinase assay the phosphatase should exhibit minimal activity towards the substrate to be phosphorylated and the phosphatase should exhibit higher activity for the substrate after it is phosphorylated by the kinase. In some embodiments, it is desired that the phosphatase shows minimal activity towards ATP, and such phosphatases have been described in the literature (e.g., Arch. Biochem. Biophys. (1978), 191(2), 613-624). In some embodiments of the invention, it is desired that the phosphate sensor is insensitive to the presence of substrate.

Some methods of the present invention include using control reactions, e.g., to make a quantitative and/or qualitative measure in an assay. In some embodiments, a reaction is compared to results from previous assays and control reactions are not performed at the same time as the sample is assayed. Control reactions include, but are not limited to, those missing a component of the assay or reaction and those that contain a known amount of a component (e.g. a positive control and/or for quantitative measurements). Control reactions include some but not all of the components of a reaction, measuring the reaction, and then adding the rest of the components and allowing the reaction to proceed and then measured the reaction. For example, in an assaying that measures a ligand using a ligand binding molecule of the invention, all of the components can be added except for the sample containing the ligand. Then a measurement can be recorded, e.g., as a negative control and/or baseline. Then the ligand can be added and then (e.g., after a period of time) a measurement is taken which relates to the amount of ligand.

In some embodiments, a "phosphate mop" is used to reduce the background levels of phosphate and/or to remove phosphate slowly from the phosphate binding protein, thus leaving the binding site free to detect phosphate (e.g., Pi) which may be released into the assay system. This can ensure that phosphate binding by the modified PBP is transient. Permanent binding may reduce the useful life of an assay system as eventually all the phosphate binding protein binding sites would become occupied (e.g., saturated). In one embodiment, the phosphate mop is an enzymatic system. In some embodiments, a 7-methyl guanosine and purine nucleoside phosphorylase system is utilized. In some embodiments, a MESG (2-amino-6-mercapto-7-methylpurine ribonucleoside) is utilized. In some embodiments, a modified version of 7-methylguanosine-based reaction including the addition of phosphodeoxyribomutase is utilized.

According to another aspect of the invention, there is provided a modified ligand binding protein (e.g., a phosphate binding protein) according to the invention for use in the measurement of a ligand (e.g., phosphate such as Pi) in the diagnosis of a disease. Some embodiments of the invention may be used to determine phosphate (e.g., Pi) or another ligand in methods of diagnosis practiced in vitro or in vivo in a human or animal.

Many methods of the invention involve measuring RET from a ligand binding molecule (e.g., a modified ligand binding molecule) and the amount of RET differs between the ligand bound and unbound ligand binding molecule. In one embodiment of the invention, (a) a ligand binding molecule (e.g., a modified ligand binding molecule) is added to a solution; (b) RET is measured; (c) the test sample is added to the solution; and (d) RET is measured. In some embodiments, the RET measured in (b) is compared to (d) to determine the presence, if any, of ligand in the test sample. In some embodiments, the test sample solution of (c) is incubated for a period of time to allow binding of the ligand binding molecule (e.g., a modified ligand binding molecule) to any ligand in the test sample. In some embodiments, (d) involves measuring RET at multiple time points, e.g., a real time assay.

Some embodiments of the invention provide a method comprised of (a) a first solution comprised of a test sample and a ligand binding molecule (e.g., a modified ligand binding molecule); (b) at least one control reaction comprised of the ligand binding molecule (e.g., a modified ligand binding molecule) and a known concentration of ligand; and (c) measuring RET in both (a) and (b). "Known concentration" as referred to in (b) can be any concentration including no ligand. In some embodiments, the RET measured in (a) is compared to the RET measured in (b). In some embodiments, the method comprises multiple control samples, each comprising various known amounts of ligand. The concentration of ligand in (a) can be determined by comparing the measured RET of (a) to the measured RET from multiple control samples, e.g., by using a standard curve determined from the multiple control samples. In some embodiments, (c) involves measuring RET at multiple time points, e.g., a real time assay. In some embodiments, (a) and (b) are incubated for a period of time to allow binding of the ligand binding molecule to any ligand in the test sample.

Many methods of the invention involve measuring RET from a modified ligand binding molecule (e.g., a PBP) and the amount of RET differs between the ligand (e.g., phosphate) bound and unbound modified ligand binding molecule (e.g., a PBP). In one embodiment of the invention, (a) the modified ligand binding molecule is added to a solution; (b) RET is measured; (c) the test sample is added to the solution; and (d) RET is measured. In some embodiments, the RET measured in (b) is compared to (d) to determine the presence, if any, of the ligand (e.g., phosphate) in the test sample. In some embodiments, the test sample solution of (c) is incubated for a period of time to allow binding of the modified ligand binding molecule (e.g., a PBP) to any ligand in the test sample. In some embodiments, (d) involves measuring RET at multiple time points, e.g., a real time assay.

Some embodiments of the invention provide a method comprised of (a) a first solution comprised of a test sample and a modified ligand binding molecule (e.g., a PBP); (b) at least one control reaction comprised of the modified ligand binding molecule (e.g., a PBP) and a known concentration of ligand (e.g., phosphate); and (c) measuring RET in both (a) and (b). "Known concentration" as referred to in (b) can be any concentration including no ligand. In some embodiments, the RET measured in (a) is compared to the RET measured in (b). In some embodiments, the method comprises multiple control samples, each comprising various known amounts of ligand. The concentration of ligand (e.g., phosphate) in (a) can be determined by comparing the measured RET of (a) to the measured RET from multiple control samples, e.g., by using a standard curve determined from the multiple control samples. In some embodiments, (c) involves measuring RET at multiple time points, e.g., a real time assay. In some embodiments, (a) and (b) are incubated for a period of time to allow binding of the modified ligand binding molecule (e.g., a PBP) to any ligand (e.g., phosphate) in the test sample.

As discussed herein, ratiometric measurements may be used for some methods/assays of the invention. In one embodiment, ratiometric measurements are made by comparing the emission (e.g. a particular or band of wavelengths of light) of both the donor and acceptor moieties.

In some embodiments, only the emission of the donor moiety is measured. As RET changes (e.g., due to phosphate binding), so can the measurable emission from the donor moiety. Without wishing to be limited by theoretical considerations, the detectable emission from the donor moiety can change due to a change in RET because if RET increases more energy is transferred from the donor to the acceptor (e.g., quenching of the donor) and therefore less detectable energy (e.g., light) is directly emitted from the donor. If RET decreases, less energy is transferred from the donor to the acceptor and therefore more detectable energy (e.g., light) is directly emitted from the donor.

In some embodiments, a luminescent reference compound may be added to the sample, and the analyte-specific signal may be referenced relative to the signal from the reference compound or from the reference compound and the sensor. In some embodiments, the luminescent reference compound may be a luminescent terbium chelate or cryptate. In some embodiments, the luminescent reference compound may be a luminescent europium chelate or cryptate The strategy of adding a reference fluorophore to a sample in order to provide for an internal calibrator has been described in the literature. (Astill et al., *Clin. Chem.* 33:1554-1557 (1987).)

Assays and methods of the invention can be comprised of various formats. Some assays and methods of the invention can optionally comprise "controls". In this aspect, a control can, for example, be a sample of known characteristics or of unknown characteristics that is used as a standard. The controls can comprise multiple samples or be a single sample. In some embodiments, the methods comprise multiple controls which can be used to establish a standard curve, which can be utilized to determine the concentration of a compound in a test sample. In some embodiments, the control reaction(s) is performed in a separate container (e.g., a tube, well, etc.) from the reaction. In some embodiments, the control reaction(s) is performed in the container as a test reaction. For example, a well can be loaded with everything except the test compound and a RET measurement is recorded, e.g., as the negative control well. Then the test compound is added to the well and subsequently a RET measurement is recorded. In some embodiments, the control wells or containers are separate from the test reactions/samples. For example, one plate (e.g., a 96 well plate) may have several wells with various concentrations (e.g., known concentrations) of the compound to be detected (e.g., phosphate, phosphatase, kinase, phosphodiesterase, etc.). Another well or set of wells may contain none of the compound to be detected. Another well or set of wells can contain the test reactions, e.g., that have an unknown concentration of the compounds to be detected.

In some assays, reactions and methods of the invention the concentration of ligand binding molecule (e.g., a modified ligand binding molecule) or PBP (e.g., modified) is about 0.1 nM to 100 nM, about 1 nM to 10 nm, about 5 nM, about 7 nM or about 2 nM. In some embodiments, the detection mode is TR-FRET, e.g., providing methods to detect phosphate in high throughput screens. In some embodiments, the methods of the invention comprise assays to determine a test compounds effect on a phosphate based assay, e.g., as described herein. These assays may directly produce or decrease phosphate (e.g., Pi) or may be coupled to an assay that produces or decreases phosphate levels.

The modified ligand binding molecules (e.g., a PBPs) of the present invention also provide reagents, methods and assays for identifying modulators of ligand (e.g., phosphate) related reactions. The modified ligand binding molecules (e.g., PBPs) of the present invention also provide reagents, methods and assays for measuring the modulation and/or changes in ligand (e.g., phosphate) related reactions. Phosphate related reactions include, but are not limited to, those involving a phosphatase, a kinase, a phosphodiesterase, prenyl transferase, phosphorylase and any reaction that produces, removes or consumes phosphate (e.g., Pi).

One embodiment of the invention provides a method for measuring kinase activity of a compound or sample comprising: a) contacting the compound or sample and a phosphorylation substrate for the kinase activity, b) contacting (a) with a phosphatase capable of removing a phosphate potentially added by the kinase activity of the compound or sample; c) contacting (b) with a modified PBP comprising a RET pair; and d) measuring RET. In some embodiments, (c) is exposed to a wavelength or wavelengths of light that excite the donor moiety. In some embodiments, (a), (b), and (c) are carried out simultaneously. For example, one solution comprising the compound, the phosphorylation substrate, the phosphatase capable of dephosphorylating the phosphorylated substrate and the modified PBP is utilized. This solution can be allowed to incubate for a period of time and then RET is measured. In another embodiment, RET is measured in real time or as kinetic measurements. In some embodiments, (a), (b), (c) or any combination thereof includes a phosphate mop. In some embodiments, a potential modulator of the kinase activity of the compound can be included in (a). Therefore, potential modulators of kinase activity can be screened or determined utilizing the methods of the invention. In some embodiments, RET is measured in (a) and/or (b). Additionally, control reactions can be set-up in the same format. Control reactions will typically have a known amount of a particular component involved in the reaction.

One embodiment of the invention provides a method for measuring kinase activity of a compound or sample comprising: a) a solution comprising the compound or sample, a phosphorylation substrate for the kinase activity, a phosphatase capable of removing a phosphate potentially added by the kinase activity of the compound or sample, and a modified PBP comprising a RET pair; and b) measuring RET. This solution can be allowed to incubate for a period of time and then RET is measured. In another embodiment, RET is measured in real time or as kinetic measurements. In some embodiments, (a) includes a phosphate mop. In some embodiments, a potential modulator of the kinase activity of the compound can be included in (a). Therefore, potential modulators of kinase activity can be screened or determined utilizing the methods of the invention. Additionally, control reactions can be set-up in the same format. Control reactions will typically have a known amount of a particular component involved in the reaction.

A phosphodiesterase (PDE) is an enzyme that catalyzes the hydrolysis of phosphodiester bonds. PDEs are responsible for the degradation of the cyclic nucleotides cAMP and cGMP. They are therefore important regulators of signal transduction mediated by these molecules Inhibitors of PDE can prolong or enhance the effects of physiological processes mediated by these cyclic nucleotides.

One embodiment of the invention provides a method for measuring phosphodiesterase activity of a compound or sample comprising: a) contacting the compound or sample and a phosphodiesterase substrate (e.g., cAMP), b) contacting (a) with a phosphatase capable of removing a phosphate that is no longer part of a phosphodiester bond on the substrate; c) contacting (b) with a modified PBP comprising a RET pair; and d) measuring RET. In some embodiments, (c) is exposed to a wavelength or wavelengths of light that excite the donor moiety. In some embodiments, (a), (b), and (c) are carried out simultaneously. For example, one solution comprising the compound or sample, the phosphodiesterase substrate, the phosphatase and the modified PBP is utilized. In one embodiment, this solution can be allowed to incubate for a period of time and then RET is measured. In another embodiment, RET is measured in real time or as kinetic measurements. In some embodiments, (a), (b), (c) or any combination thereof includes a phosphate mop. In some embodiments, a potential modulator of the phosphodiesterase activity of the compound can be included in (a). Therefore, potential modulators of phosphodiesterase activity can be screened or determined utilizing the methods of the invention. In some embodiments, RET is measured in (a) and/or (b). Additionally, control reactions can be set-up in the same format. Control reactions will typically have a known amount of a particular component involved in the reaction.

The invention also provides methods to measure and/or detect competitive binding of a compound with a ligand binding molecule and a ligand. For example as described in, a modified ligand binding molecule can be used to detect binding to a ligand. The assays and methods of the invention can further include a compound and the compound can be determined whether it is a modulator of binding of the ligand to the ligand binding molecule. For example, it may be desirable to determine if a compound modulates (e.g., inhibits or increases) binding of a ligand to a ligand binding molecule. The compound can be added to a reaction comprising a ligand binding molecule of the invention and a ligand. In some embodiments, modulation is detected by comparing the RET of a reaction with the compound to one without. In some embodiments, differences in RET can be used to determine if the compound is a modulator. Multiple compounds can be tested at one time, e.g., in one reaction or in separate reactions for each compound. Additionally, the invention provides methods and assays for screening (e.g., libraries of) compounds for modulating binding of a ligand for a ligand binding molecule. Additionally, the invention provides methods and assays for screening (e.g., libraries of) compounds that bind a ligand binding molecule. In other words, not necessarily determining if the compound modulates binding of a ligand to the ligand binding molecule, but determining if the compound itself is capable of binding the ligand binding molecule, e.g., in a similar way as a known ligand.

One embodiment of the invention provides a method for measuring phosphodiesterase activity of a compound or sample comprising: a) contacting the compound or sample, a phosphodiesterase substrate (e.g., cAMP), a phosphatase capable of removing a phosphate that is no longer part of a phosphodiesters bond on the substrate; and a modified PBP comprising a RET pair; and b) measuring RET. This solution can be allowed to incubate for a period of time and then RET is measured. In another embodiment, RET is measured in real time or as kinetic measurements. In some embodiments, (a) includes a phosphate mop. In some embodiments, a potential modulator of the phosphodiesterase activity of the compound can be included in (a). Therefore, potential modulators of phosphodiesterase activity can be screened or determined utilizing the methods of the invention. Additionally, control reactions can be set-up in the same format. Control reactions will typically have a known amount of a particular component involved in the reaction.

In part, this section describes PBPs as an example of a phosphate binding molecule and ligand binding molecule. The invention is not intended to be limited to PBPs as the only ligand binding molecules that are compatible with some embodiments of the present invention. Any phosphate or ligand binding molecule can be used that undergoes a conformational change upon binding and/or release of ligand and can be labeled directly and or indirectly with detectable moieties, wherein the detectable signal changes upon the binding and/or release of the ligand.

All publications, patents and patent applications mentioned in this specification are herein incorporated by reference into the specification to the same extent as if each individual publication, patent or patent application was specifically and individually indicated to be incorporated herein by reference.

7. EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

Whereas, particular embodiments of the invention have been described herein for purposes of description, it will be appreciated by those skilled in the art that numerous variations of the details may be made without departing from the invention as described in the appended claims.

Example 1

Production of the Modified PBPs OG-PBP-Tb and Rd-PBP-Tb

Phosphate Binding Protein (PBP) mutant A197C can be produced as described (Brune et al. (1994) Biochemistry 33, 8262-8271; Brune et al. (1998) Biochemistry 37, 10370-10380). Two uL of 20 mM Oregon Green® 488 iodoacetamide (Invitrogen, Catalog#O6010) in DMF or 20 mM Rhodamine Red® C2 maleimide (Invitrogen, Cat#R6029) in DMSO was added to 50 uL of PBP A197C in 50 mM Tris pH 8.0 in the presence of 200 uM 7-methylguanosine and 0.2 Units/mL Purine Nucleoside Phosphorylase, followed by a 1 hour incubation at room temperature. The reaction products were then desalted over a NAP-5 column (GE Healthcare) essentially according to the manufacturer's protocol in 50 mM Tris pH 8.0 and collected in a 1 mL volume and then dialyzed against 100 mM sodium bicarbonate pH 9.5 overnight. The products were then concentrated in a Microcon-50 device (Millipore) to 23 uL and 12 uL for the Oregon Green and Rhodamine-labeled forms, respectively, and the concentration of each was estimated using the extinction coefficient of $60,880M^{-1}$ $cm^{-1}$. In one experiment, the concentrations were found to be 166 uM and 276 uM for the Oregon Green and Rhodamine-labeled forms, respectively.

A 3-fold molar excess of LanthaScreen™ Amine Reactive Tb Chelate (Invitrogen, Cat#PV3582) was added to each from a freshly prepared 5 mg/mL stock in 100 mM sodium bicarbonate pH 9.5. The reactions were incubated at room temperature for 2 hours. The reaction products were then desalted over a NAP-5 column (GE Healthcare) essentially according to the manufacturer's protocol in 25 mM Tris pH 8.0, 1 mM $MgCl_2$. The products of the reactions are referred to as OG-PBP-Tb and Rd-PBP-Tb for the Oregon Green and Rhodamine-labeled forms, respectively.

In this example, two different TR-FRET based phosphate sensors, OG-PBP-Tb and Rd-PBP-Tb, were produced based on fluorescently labeled forms of E. coli phosphate binding protein (PBP), SEQ ID NO:2. They were based on the single mutant PBP A197C. Both showed an increase in TR-FRET in response to phosphate.

Example 2

Production Mutant Sensors A47C/A197C, A197C/E268C, and Q201C

In this Example, one sensor is based on the modified PBP A47C/A197C, a second is based on the modified PBP A197C/E268C, and a third is based on the modified PBP Q201C.

A plasmid coding for expression of PBP A197C was modified by site-directed mutagenesis to encode for the double mutants PBP A47C/A197C and PBP A197C/E268C and the single mutant Q201C (Brune et al. (1994) Biochemistry 33, 8262-8271). BL21(DE3) E. coli cells were transformed with the plasmids and selected on LB agar plates with tetracycline (12.5 ug/mL). 10 mL cultures of LB with tetracycline (12.5 ug/mL) were inoculated with colonies from the plates and grown at 37° C. for 6 hours at 250 rpm. 5 mL from these cultures was then used to inoculate 50 mL cultures of the same media which were grown overnight at 37° C. for 6 hours at 250 rpm. 10 mL of the 50 mL cultures were used to inoculate 500 mL of TG minimal media (120 mM Tris-HCl, 80 mM NaCl, 20 mM $NH_4Cl$, 20 mM KCl, and 3 mM $Na_2SO_4$) with additives (12.5 ug/mL tetracycline, 2 g/L glucose, 0.2 mM $CaCl_2$, 10 uM $FeSO_4$, 0.2 mM $MgSO_4$, and 10 mg/L thiamine) and 640 uM $KH_2PO_4$. These 500 mL cultures were grown for approximately 6 hours to an OD595 of approximately 2, pelleted by centrifugation, and the cells were resuspended in the same media, except with 64 uM $KH_2PO_4$. The cultures were then grown for approximately 16 hours 37° C. and at 250 rpm.

The cell pellets were then harvested by centrifugation and stored at −80° C., and the media is discarded. Cell pellets from the equivalent of 500 mL of culture were suspended in 20 mL Buffer A (20 mM Tris pH 8.2, 1 mM $MgCl_2$) and centrifuged at approximately 15,000×g for 1 hour at 4° C. For PBP A197C/E268C and PBP Q201C the supernatant was decanted and loaded onto a 100 mL Q sepharose Fast Flow (GE Healthcare) column equilibrated in Buffer A. The column was washed with 2 column volumes of Buffer A and then eluted with a 2 column volume gradient, Buffer A to Buffer B (Buffer A with 200 mM NaCl) followed by 1 column volume of Buffer B. For PBP A47C/A197C, the supernatant was loaded onto a 75 mL Q Sepharose column equilibrated in Buffer A, washed with 100 mL of Buffer A, and step eluted with Buffer B. For both proteins, the fractions were analyzed by SDS-PAGE and fractions containing the ~35 kDa protein are pooled.

A sample of PBP A197C/E268C was brought to 200 uL (final concentration of 75 uM) with hepes buffered saline (HBS) (137 mM NaCl, 2.7 mM KCl, 10 mM HEPES pH7.5) and PBP A47C/A197C was left at 25 uM in a volume of 200 uL. 1.2 uL of 50 U/mL PNPase, 2 uL of 30 mM 7-methylguanosine, and 2 uL of 100 mM $MgCl_2$ were added to each sample and incubated at room temperature for 45 minutes. 0.8 parts of thiol-reactive 6-iodoacetamidofluorescein (6-IAF) (Invitrogen, Catalog#I-30452) was added from a 10 mM stock in DMSO. The reactions were incubated at room temperature for 5 hours and 30 minutes and then desalted using a NAP 5 column (GE Healthcare, Catalog#17-0853-02) into HBS following the manufacturer's protocol. For PBP A197C/E268C, 6.2 uL of 12 mM LanthaScreen™ Thiol Reactive Tb Chelate (Invitrogen, Catalog#PV3579) was added. For PBP A47C/A197C, 2.1 uL of 12 mM LanthaScreen™ Thiol Reactive Tb Chelate was added. The Tb labeling reactions were incubated for 1 hour at room temperature and desalted over a NAP-5 column (GE Healthcare, Catalog#17-0853-02) following the manufacturer's protocol. The resulting products are referred to as Sensor(47-197) and Sensor(197-268).

Example 3

Assays with OG-PBP-Tb and Rd-PBP-Tb

The fluorescence of OG-PBP-Tb and Rd-PBP-Tb (in 25 mM Tris pH 8.0, 1 mM $MgCl_2$) were assessed in 22 uL reactions containing a phosphate mop (7-methylguanosine and purine nucleoside phosphorylase), 360 uM $KH_2PO_4$, or no additional component. These reactions were performed at both 10 uM and 200 nM for OG-PBP-Tb and at 9 and 0.28 uM for Rd-PBP-Tb. The samples were excited at 340 nm (30 nm bandpass) and fluorescence intensity was captured at 520 nm (25 nm bandpass) and 495 nm (10 nm bandpass) using a 200 µs detection window followed by a 100 µs delay on a Tecan Safire2TM instrument. The TR-FRET ratio was calculated by dividing the emission intensity at 520 nm by the intensity at 495 nm.

Figure 4:
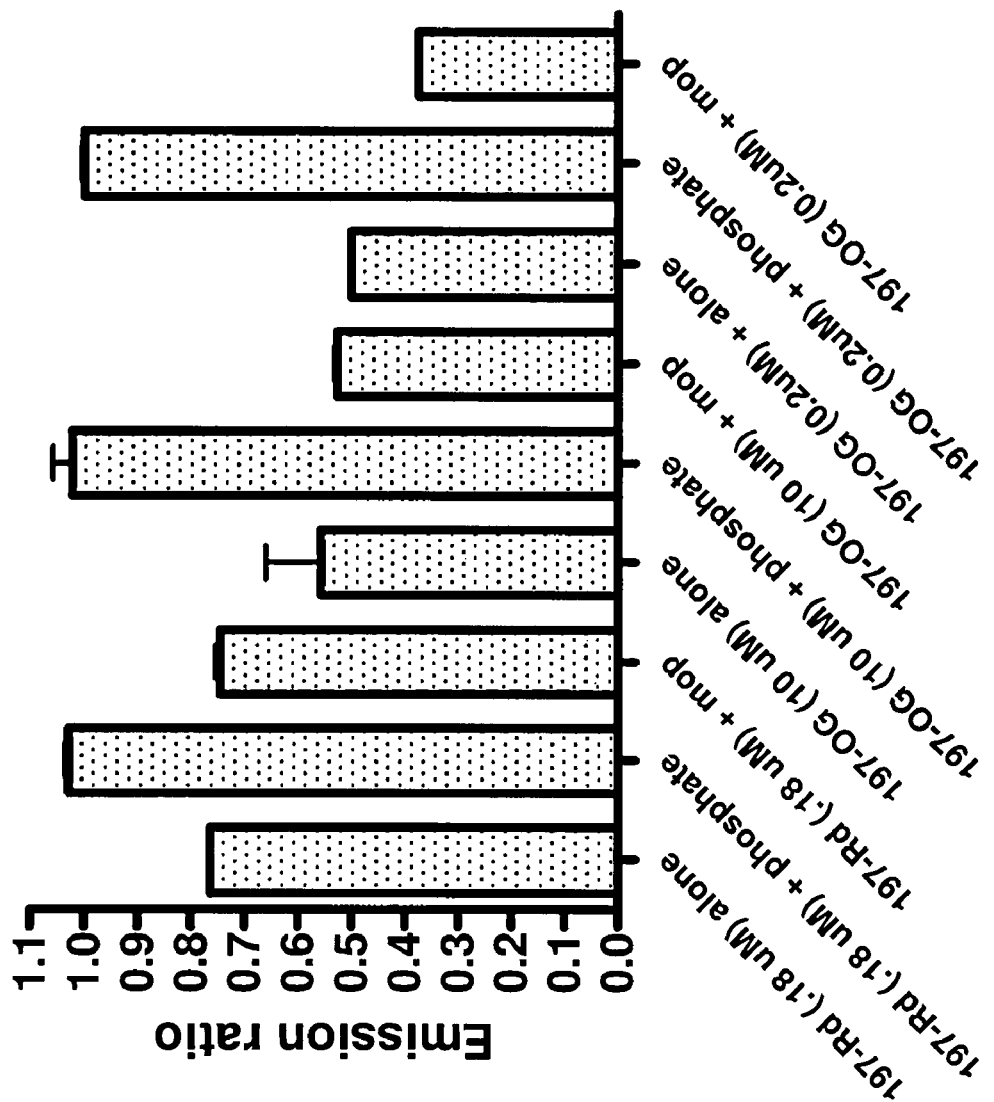
FIG. 4 shows a response of OG-PBP-Tb and Rd-PBP-Tb to phosphate.

In a set of experiments, the signals of both OG-PBP-Tb and Rd-PBP-Tb show a strong dependence on the presence of phosphate (FIG. 4).

Example 4

Assays with Tb-PBP(Q201C)-Fl 10 uL of each version of Tb-PBP(Q201C)-Fl (different amount of Tb chelate) was diluted to 100 nM with HBS and added to either 10 uL of 200 uM phosphate or to 10 uL of Phosphate Mop (0.8 mM 7-MEG, 4 U/mL PNPase, and 1 mM MgCl2). The samples were excited at 340 nm (30 nm bandpass) and fluorescence intensity was captured at 520 nm (25 nm bandpass) and 495 nm (10 nm bandpass) using a 200 µs detection window followed by a 100 µs delay on a Tecan Safire2TM instrument.

In a set of experiments, each version of Tb-PBP(Q201C)-Fl shows a strong signal dependence on phosphate (Table 1).

TABLE 1

| Sample | Emission ratio with phosphate | Emission ratio with Mop | Fold-change in signal (emission ratio with phosphate/ratio with Mop) |
|---|---|---|---|
| Tb-PBP(Q201C)-Fl labeled with 3 parts Tb chelate | .72 | .23 | 3.06 |
| Tb-PBP(Q201C)-Fl labeled with 7 parts Tb chelate | .78 | .28 | 2.77 |
| Tb-PBP(Q201C)-Fl labeled with 10 parts Tb chelate | .83 | .31 | 2.65 |
| Tb-PBP(Q201C)-Fl labeled with 20 parts Tb chelate | .85 | .34 | 2.48 |

Example 5

Assays with Double Mutant Sensor(47-197) and Sensor(197-268)

Figure 5:
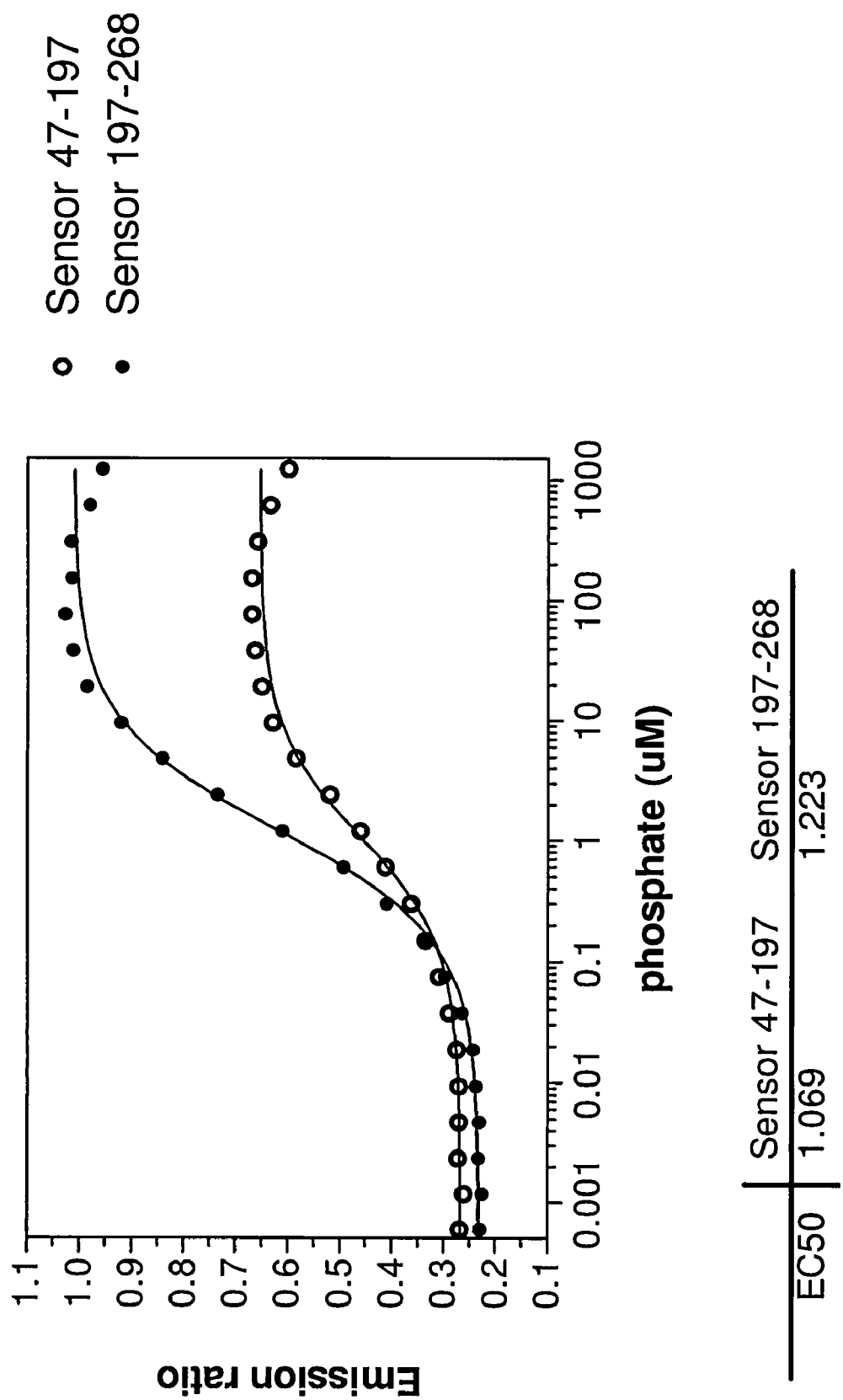
FIG. 5 shows a titration of phosphate against double mutant phosphate sensors.

The sensors were first incubated for 1 hour with 0.0039 Units/mL Purine Nucleoside Phosphorylase and 0.4 mM 7-methylguanosine, and 0.5 mM $MgCl_2$ to remove any residual or contaminating phosphate. 10 uL of each sensor (approximately 100 nM) was added to 10 uL of phosphate standards (final concentrations of 1250, 625, 313, 156, 78, 39, 20, 9.8, 2.4, 1.2, 0.61, 0.31, 0.15, 0.076, 0.038, 0.019, 0.0095, 0.0048, 0.0024, 0.0012, 0.00060, 0.00030, and 0.000149 uM. The samples were excited at 340 nm (30 nm bandpass) and fluorescence intensity was captured at 520 nm (25 nm bandpass) and 495 nm (10 nm bandpass) using a 200 µs detection window followed by a 100 µs delay on a Tecan Ultra instrument. The TR-FRET ratio was calculated by dividing the emission intensity at 520 nm by the intensity at 495 nm Results from a set of experiments are shown in FIG. 5.

Example 6

A Phosphatase Assay

PTP1B is a protein tyrosine phosphatase that negatively regulates insulin signaling by dephosphorylating the insulin receptor.

Figure 6:
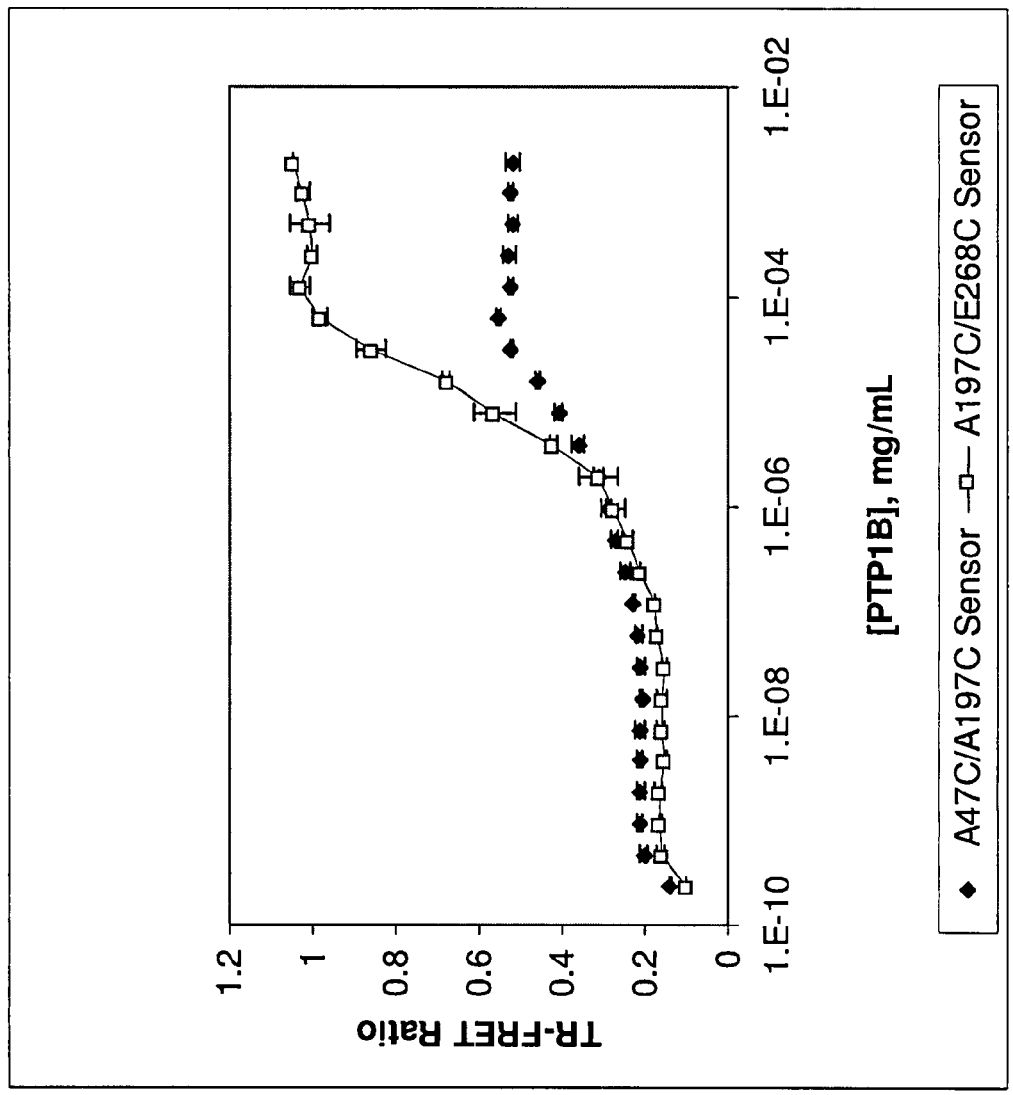
FIG. 6 shows detection of phosphatase activity with double mutant sensors.

PTP1B (Invitrogen, Product#P3079) a recombinant human full-length protein, histidine-tagged, expressed in insect cells) was serially diluted across a plate in 25 mM BisTris Propane in a 5 uL volume and incubated for 30 minutes at room temperature in the presence of 1 U/mL PNPase, 400 uM 7-methylguanosine, and 100 nM Sensor(47-197) or Sensor(197-268). Then, 10 uL of a PTP1B substrate (Biomol; Plymouth Meeting, Pa.; Catalog#P-323) was added to a final concentration of 50 uM. After an approximately 1 hour incubation, the samples were excited at 340 nm (30 nm bandpass) and fluorescence intensity was captured at 520 nm (25 nm bandpass) and 495 nm (10 nm bandpass) using a 200 µs detection window followed by a 100 μs delay on a Tecan Ultra instrument. The TR-FRET ratio was calculated by dividing the emission intensity at 520 nm by the intensity at 495 nm Results from a set of experiments are shown in FIG. 6.

Example 7

A Phosphodiesterase Assay

Some embodiments of the invention relate to the detection of phosphodiesterase activity. Exemplary assays and their details and results are outlined below.

6.1 Demonstration of Lack of Modified PBP response to Substrates.

Six different phosphate esters (phospho-serine (pSer), phospho-threonine (pThr), phospho-tyrosine (pTyr), p-nitrophenyl phosphate (PNP), adenosine monophosphate (AMP), and guanosine monophosphate (GMP)), two phosphodiesters (cyclic AMP (cAMP) and cyclic GMP (cGMP)), in addition to phosphate as a positive control, were titrated against 1 uM coumarin labeled PBP (Invitrogen, Carlsbad, Calif., part#PV4406) (starting at 200 uM compound concentration), and fluorescence was measured (excite 430/5, emit 450/5).

Figure 7:
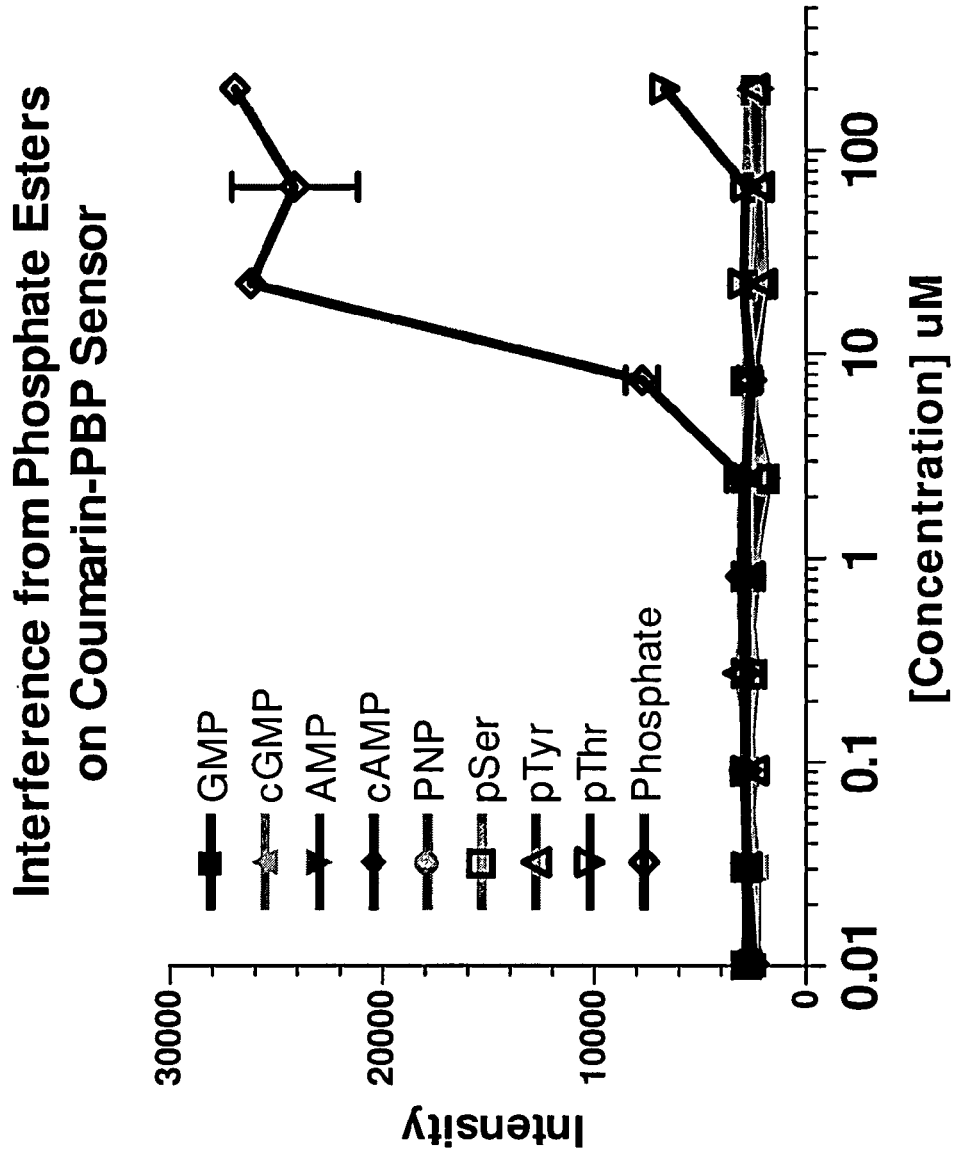
FIG. 7 shows the level of interference, if any, from various phosphate esters using a coumarin-PBP sensor. Experimental procedures are described in Example 6.1.

The results from a set of experiments are shown in FIG. 7. None of the phosphate esters or phosphodiesters showed appreciable response in the assay.

6.2 Demonstration of Cleavage of Phosphate Esters in Presence of Phosphatase

To demonstrate cleavage of the phosphate esters in the presence of phosphatase, and insensitivity of the phosphodiesters (cAMP, cGMP) to phosphatase, a large excess (8 units per 20 uL assay well) of recombinant bovine alkaline phosphatase (Sigma, Cat#P8361) was added to each well containing >1 uM compound and allowed to incubate 5 minutes before measuring fluorescence intensity as described.

Figure 8:
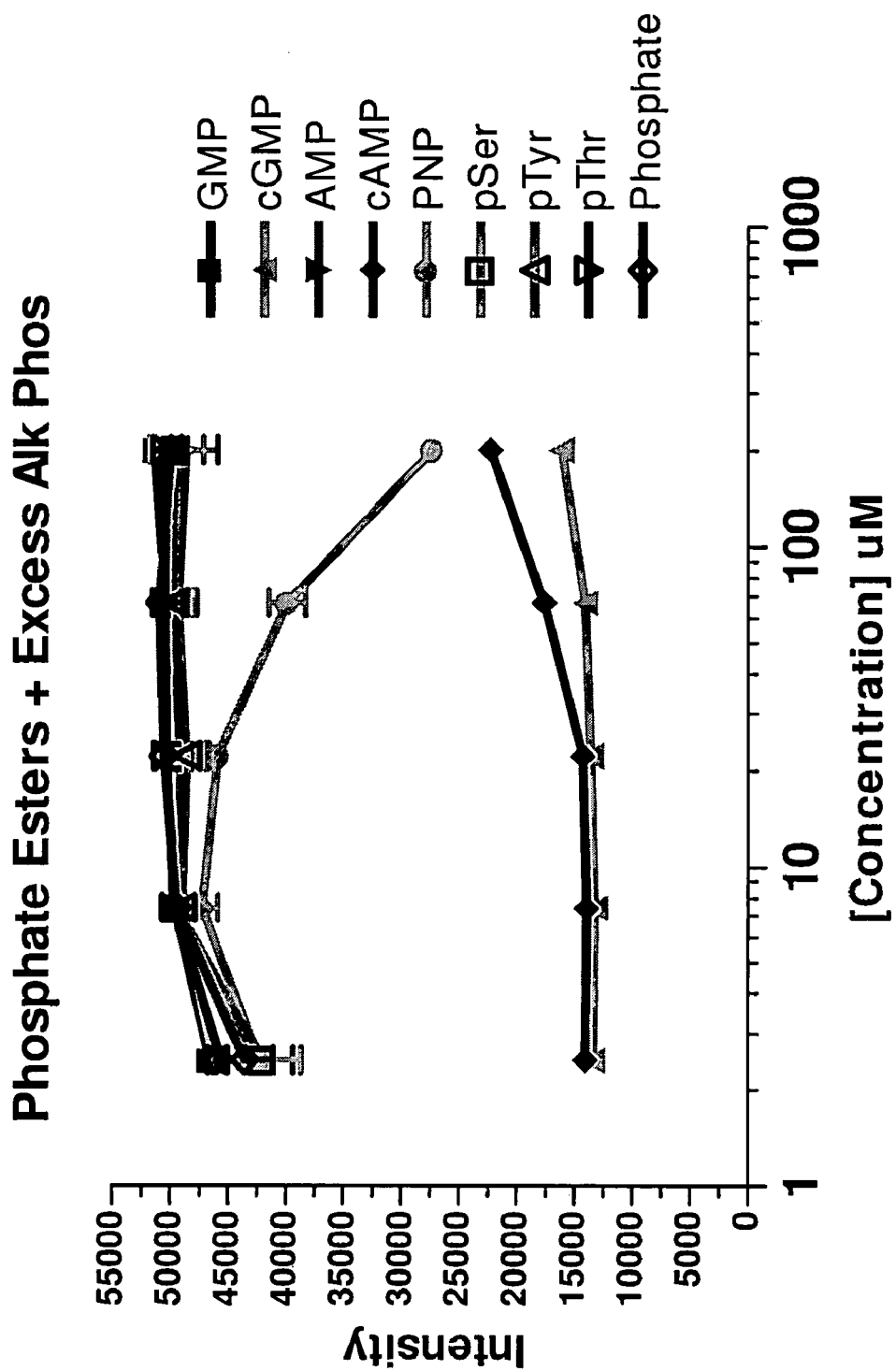
FIG. 8 shows cleavage of the phosphate esters in the presence of phosphatase, and insensitivity of the phosphodiesters (cAMP, cGMP) to phosphatase. Experimental procedures are described in Example 6.2.

In a set of experiments, all of the phosphate monoesters showed sharp increases in fluorescence intensity, indicating full cleavage by phosphatase. The results are shown in FIG. 8. PNP showed a decrease in intensity at higher phosphatase concentrations due to the fact that the product of the dephosphorylation strongly absorbs light. cAMP and cGMP showed some increase in fluorescent intensity, but the amount of increase was minimal relative to the phosphate monoesters.

6.3 Determining Minimal Amount of Phosphatase to Rapidly Cleave Phosphate Monoesters To determine the minimal amount of phosphatase necessary to rapidly cleave the phosphate monoesters, alkaline phosphatase was titrated against the same set of phosphate mono- and di-esters (less PNP), as well as ATP, and fluorescence intensity was measured over the course of one hour.

Figure 9A:
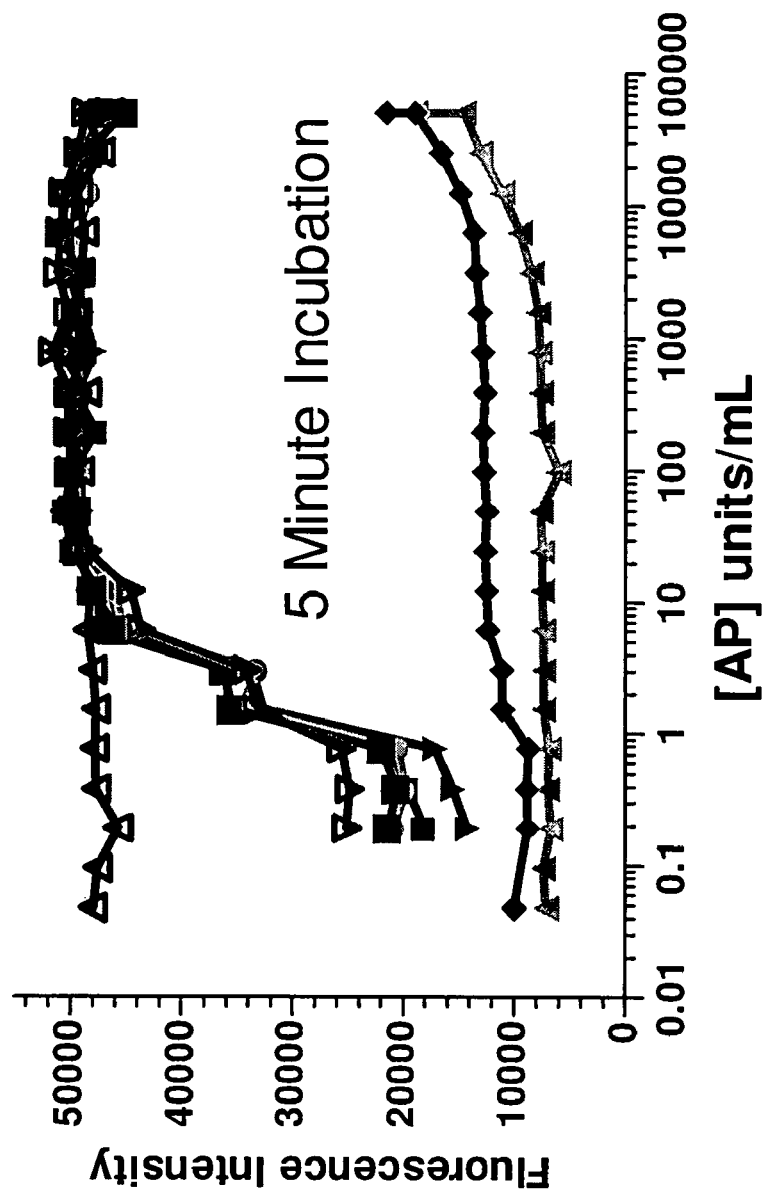
FIG. 9 shows results where alkaline phosphatase is titrated against the same set of phosphate mono- and di-esters (less PNP), as well as ATP, and fluorescence intensity is measured over the course at 5 minutes (FIG. 9A) or one hour (FIG. 9B). Experimental procedures are described in Example 6.3.
Figure 9B:
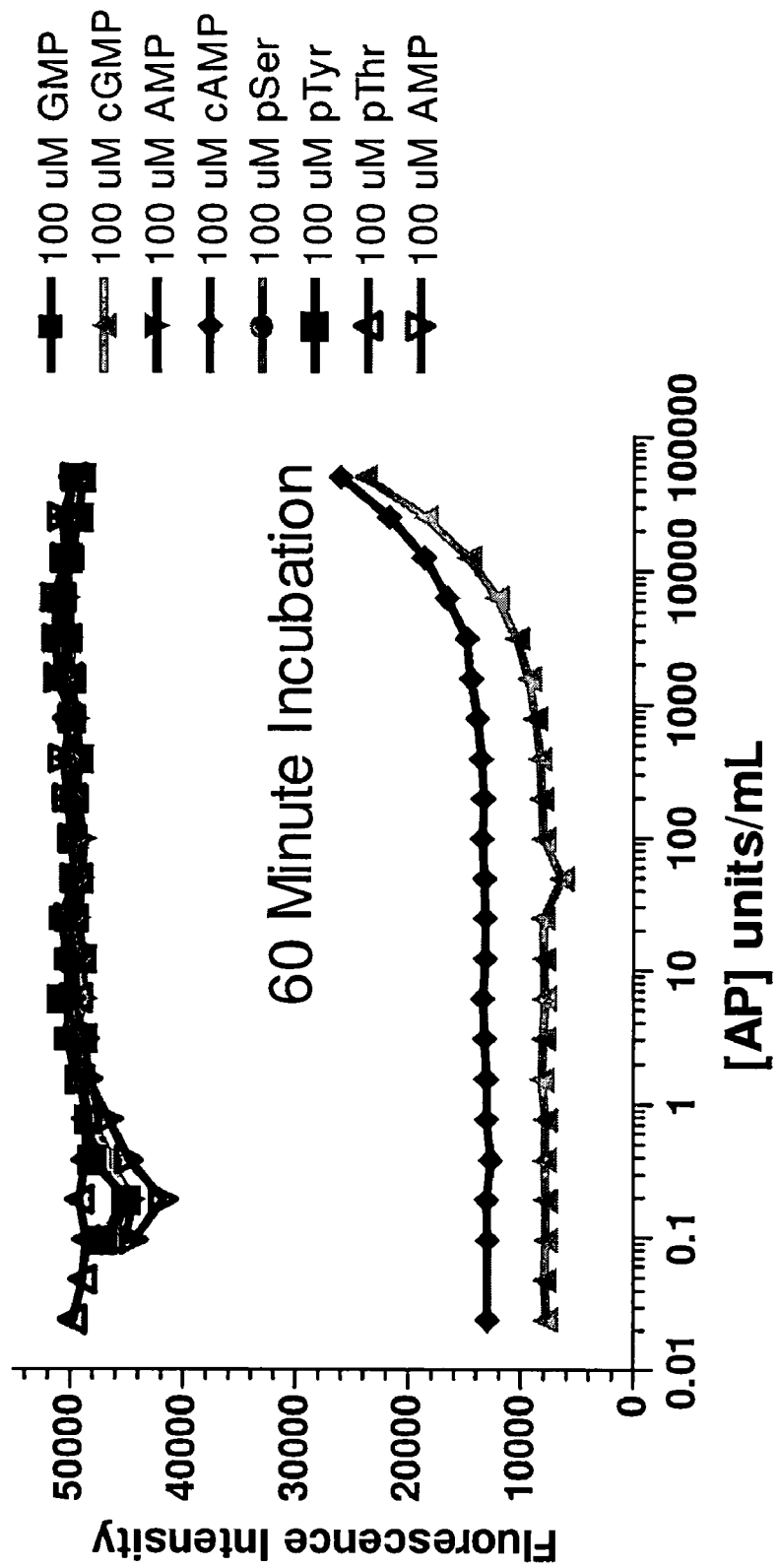

Data from 5 minute and 1 hour time points are shown in FIGS. 9A and 9B, respectively. It can be seen that within 5 minutes, 10 milli-units/mL of alkaline phosphatase cleaved 100 μM phosphate monoesters (or ATP) but did not cleave phosphodiesters such as cAMP or cGMP. After one hour there was no detectible activity on cAMP or cGMP up to about 1 unit/mL alkaline phosphatase.

6.4 Detection of Phosphodiesterase Activity Against cAMP or cGMP as a Substrate

To demonstrate the utility of the invention in the detection of phosphodiesterase activity against cAMP or cGMP as a substrate, a titration of calmodulin-sensitive phosphodiesterase from bovine brain (Sigma, Cat#P9529) was incubated with 100 uM cAMP or cGMP in the presence of 1 uM coumarin-PBP (Invitrogen, Carlsbad, Calif., part#PV4406), 10 uM $Ca^{2+}$, with or without 1 unit/mL alkaline phosphatase and 1 unit/mL calmodulin (Sigma, Cat#P2277). The plate was read (e.g., after a one hour incubation).

The data from one set of experiments using cAMP and cGMP are shown in FIGS. 10A and 10B, respectively.

With either cAMP or cGMP as a substrate, intensity was seen to be sensitive to the amount of phosphodiesterase present, as well as the presence of alkaline phosphatase (an absolute requirement) and calmodulin (the rate was increased in the presence of calmodulin). The amount of calmodulin used in this experiment was not optimal, and an increase in calmodulin concentration would be expected to show a more pronounced effect.

The above experiment was also performed in "kinetic mode", and the plate read every two minutes. When the rate of the reaction (slope for the first ~30% of the reaction) was plotted versus enzyme, there was a linear relationship between rate and the concentration of enzyme, suggesting the suitability of this format for both HTS as well as more detailed kinetic analyses of phosphodiesterase catalyzed hydrolysis of phosphodiesters. Results from one experiment are shown in FIG. 11.

Example 8

Production of Fl-PBP-Tb 268 uL of 113 uM A197C PBP was diluted with 113 uL of HBS (137 mM NaCl, 2.7 mM KCl, 10 mM HEPES pH7.5). 15.75 μL of 10 mM 6-iodoacetamidofluorescein (Invitrogen Part#130452) in DMSO was added. Phosphate mopping reagents were then added (1.2 μL of PNPase, 2 μL of 7-MEG, and 2 μL of 100 mM $MgCl_2$) to sequester phosphate. This reaction was incubated at room temperature for 2.5 hours and then desalted with a NAP-5 column (GE Healthcare) into HBS following the manufacturer's protocol. 10 μL of 1 mM LanthaScreen™ Amine Reaction Tb Chelate (Invitrogen Part#PV3582) in 1 M sodium bicarbonate pH 9.5 was then added 200 μL of the desalted product and incubated at room temperature overnight. The material was then desalted with a NAP-5 column into HBS, producing Fl-PBP-Tb [Fl-PBP (A197C)-Tb(amine)].

Example 9

Assays with Fl-PBP-Tb

Add 10 μL of twenty-four phosphate standards (with phosphate at 2 mM, 1 mM, 500 μM, 250 μM, 125 μM, . . . ) to 10 μL of 100 nM Fl-PBP-Tb (in 10 mM Tris pH 7.6, 0.05% Triton X-100) in a 384-well plate (Corning 3677). The same series of reactions was also performed with 100 nM Fl-PBP-Tb that also had either 10 nM or 100 nM of a Eu-labeled Antibody produced by standard methods with an amine-reactive TTHA-based Eu-chelate. The samples were excited at 340 nm (30 nm bandpass) and fluorescence intensity was captured at 520 nm (25 nm bandpass), 495 nm (10 nm bandpass), and 615 nm using a 200 μs detection window followed by a 100 μs delay on a Tecan Ultra instrument. Response as a function of phosphate concentration was presented either by 520 nm emission, or the ratio or emission at 520 nm to 615 nm. Results are presented in FIGS. 13-15.

The invention claimed is:

1. A phosphate binding protein comprising a resonance energy transfer (RET) pair of moieties comprised of at least one donor moiety and at least one acceptor moiety, wherein the donor moiety comprises a lanthanide metal complex, wherein neither the donor nor acceptor moiety is a fluorescent protein, and wherein the phosphate binding protein is capable of binding inorganic phosphate and wherein the binding results in a change in RET.

2. The protein of claim 1, wherein the distance or orientation between the at least two moieties is altered upon binding the phosphate.

3. The protein of claim 1, wherein the RET pair is capable of time resolved RET.

4. The protein of claim 1, wherein the at least one acceptor moiety is selected from the group consisting of a fluorescein, a rhodamine, a FITC, a 5-carboxyfluorescein, a 6-carboxyfluorescein, a 7-hydroxycoumarin-3-carboxamide, a 6-chloro-7-hydroxycoumarin-3-carboxamide, a fluorescein-5-isothiocyanate, a dichlorotriazinylaminofluorescein, a tetramethylrhodamine-5-isothiocyanate, tetramethylrhodamine-6-isothiocyanate, a succinimidyl ester of 5-carboxyfluorescein, a succinimidyl ester of 6-carboxyfluorescein, a 5-carboxytetramethylrhodamine, a 6-carboxymethylrhodamine, a 7-amino-4-methylcoumarin-3-acetic acid, 6-IAF, 5-IAF, fluorescein-5-maleimide, and 5-(bromomethyl)fluorescein.

5. The protein of claim 1, wherein the lanthanide metal complex comprises an organic antenna moiety, a metal liganding moiety and a lanthanide metal ion.

6. The protein of claim 5, wherein the lanthanide metal ion is selected from the group consisting of: Sm(III), Ru(III), Eu (III), Gd(III), Tb(III), and Dy(III).

7. The protein of claim 5, wherein the organic antenna moiety is selected from the group consisting of: rhodamine 560, fluorescein 575, fluorescein 590, 2-quinolone, 4-quinolone, 4-trifluoromethylcoumarin (TFC), 7-diethyl-aminocoumarin-3-carbohydrazide, 7-amino-4-methyl-2-coumarin (carbostyril 124), 7-amino-4-methyl-2-coumarin (coumarin 120), 7-amino-4-trifluoromethyl-2-coumarin (coumarin 124), and aminomethyltrimethylpsoralen.

8. The protein of claim 5, wherein the metal liganding moiety is a metal chelating moiety selected from the group consisting of: EDTA, DTPA, TTHA, DOTA, NTA, HDTA, DTPP, EDTP, HDTP, NTP, DOTP, DO3A, DOTAGA, and NOTA.

9. The protein of claim 1, wherein the lanthanide metal complex has a structure:

$$-L_n-A-S_n-C_M,$$

or $$-L_n-C_M-S_n-A,$$

wherein A represents an organic antenna moiety;
L represents a linker;
S represents a spacer;
n can be 0 or 1;
C represents a metal chelating moiety; and
M represents a lanthanide metal ion coordinated to C.

10. The protein of claim 1, wherein the protein has at least one non-native cysteine amino acid and the first or second moiety is attached to the non-native cysteine amino acid.

11. The protein of claim 10, wherein the protein comprises a modified amino acid sequence of the phosphate binding protein encoded by the phoS gene.

12. The protein of claim 1, wherein the amino acid sequence of the protein is SEQ ID NO:1 or SEQ ID NO:2.

13. The protein of claim 1, wherein the phosphate binding protein comprises an amino acid sequence 90% homologous to SEQ ID NO:1 or SEQ ID NO:2.

14. The protein of claim 13, wherein the protein has at least one non-native cysteine amino acid.

15. The protein of claim 13, comprising an amino acid substitution selected from the group consisting of A47C, A197C, Q201C and E268C of SEQ ID NO:2.

16. The protein of claim 1, wherein the at least one donor moiety is linked to the phosphate binding protein via an amine or thiol linkage.

17. The protein of claim 1, wherein the at least one acceptor moiety is linked to the phosphate binding protein via an amine or thiol linkage.

18. The protein of claim 13, comprising at least 2 amino acid substitutions selected from the group consisting of A197C/E268C, A47C/A197C, A47C/E268C, Q201C/E268C, A47C/Q201C, and A197C/Q201C of SEQ ID NO:2.

19. The protein of claim 12, wherein the at least one donor moiety or the at least one acceptor moiety is linked to the protein at a region selected from the group consisting of amino acids 42-51 of SEQ ID NO:2, amino acids 149-159 of SEQ ID NO:2, amino acids 180-191 of SEQ ID NO:2, amino acids 192-201 of SEQ ID NO:2 and amino acids 264-273 of SEQ ID NO:2.

20. The protein of claim 13, wherein the at least one donor moiety or the at least one acceptor moiety is linked to the protein at a region selected from the group consisting of amino acids 42-51 of SEQ ID NO:2, amino acids 149-159 of SEQ ID NO:2, amino acids 180-191 of SEQ ID NO:2, amino acids 192-201 of SEQ ID NO:2 and amino acids 264-273 of SEQ ID NO:2.

* * * * *